(12) United States Patent
Morere et al.

(10) Patent No.: US 10,894,803 B2
(45) Date of Patent: Jan. 19, 2021

(54) MULTI-FUNCTIONALIZED POLYSACCHARIDE COMPOUNDS AND USE THEREOF FOR TARGETING THE CATION-INDEPENDENT MANNOSE 6-PHOSPHATE RECEPTOR

(71) Applicants: NANOMEDSYN, Montpellier (FR); CENTRE NATIONAL DE LA RECHERCHE SCIENTIFIQUE - CNRS, Paris (FR); UNIVERSITE DE MONTPELLIER, Montpellier (FR)

(72) Inventors: Alain Morere, Saint Gely du Fesc (FR); Afitz Da Silva, Montpellier (FR); Elise Bouffard, Mignaloux Beauvoir (FR); Khaled El Cheikh, Montpellier (FR); Jean-Olivier Durand, Palavas les Plots (FR); Marie Maynadier, Ceyras (FR); Ilaria Basile, Saint Gely du Fesc (FR)

(73) Assignees: NANOMEDSYN, Montpellier (FR); Centre National de la Recherche Scientifique, Paris (FR); Universite de Montpellier, Montpellier (FR)

( * ) Notice: Subject to any disclaimer, the term of this patent is extended or adjusted under 35 U.S.C. 154(b) by 201 days.

(21) Appl. No.: 15/759,879

(22) PCT Filed: Sep. 15, 2016

(86) PCT No.: PCT/FR2016/052339
§ 371 (c)(1),
(2) Date: Mar. 14, 2018

(87) PCT Pub. No.: WO2017/046535
PCT Pub. Date: Mar. 23, 2017

(65) Prior Publication Data
US 2018/0265534 A1 Sep. 20, 2018

(30) Foreign Application Priority Data

Sep. 18, 2015 (FR) .................................. 15 58806

(51) Int. Cl.
*C07H 15/04* (2006.01)
*C07H 15/18* (2006.01)
(Continued)

(52) U.S. Cl.
CPC ............ *C07H 15/04* (2013.01); *A61K 38/47* (2013.01); *A61K 41/0057* (2013.01);
(Continued)

(58) Field of Classification Search
None
See application file for complete search history.

(56) References Cited

U.S. PATENT DOCUMENTS

| 3,410,642 | A | 11/1968 | Chas |
| 2013/0274210 | A1 | 10/2013 | Prandi et al. |
| 2017/0029898 | A1 | 2/2017 | Garcia et al. |

FOREIGN PATENT DOCUMENTS

| EP | 2 594 575 | 5/2013 |
| FR | 2 964 107 | 3/2012 |

(Continued)

OTHER PUBLICATIONS

International Search Report and Written Opinion of the International Searching Authority dated Nov. 24, 2016, which issued during prosecution of International Application No. PCT/FR2016/052339.

(Continued)

*Primary Examiner* — Heidi Reese
(74) *Attorney, Agent, or Firm* — Morgan, Lewis & Bockius LLP

(57) ABSTRACT

The subject matter of the present invention is a compound characterized in that it has the general formula (I): in which $P^1$, X, n, A, L and $L_1$ are as defined in Claim 1. The present invention also relates to a process for preparing said compounds (I) and to the use thereof for targeting the cation-independent mannose 6-phosphate receptor (CI-M6PR). The subject matter of the invention is also a conjugate of formula (III): in which $P^1$, X, n, A, L and $L'_1$ are as defined in Claim 6, and the use thereof: —in a method for therapeutic treatment of the human or animal body, in particular chosen from enzyme replacement therapy, photodynamic therapy or cancer treatment, and/or—in a method of diagnosis, in particular of diseases or of ailments associated with an increase or with a decrease in CI-M6PR expression.

(Continued)

-continued (III)

Figure 1:
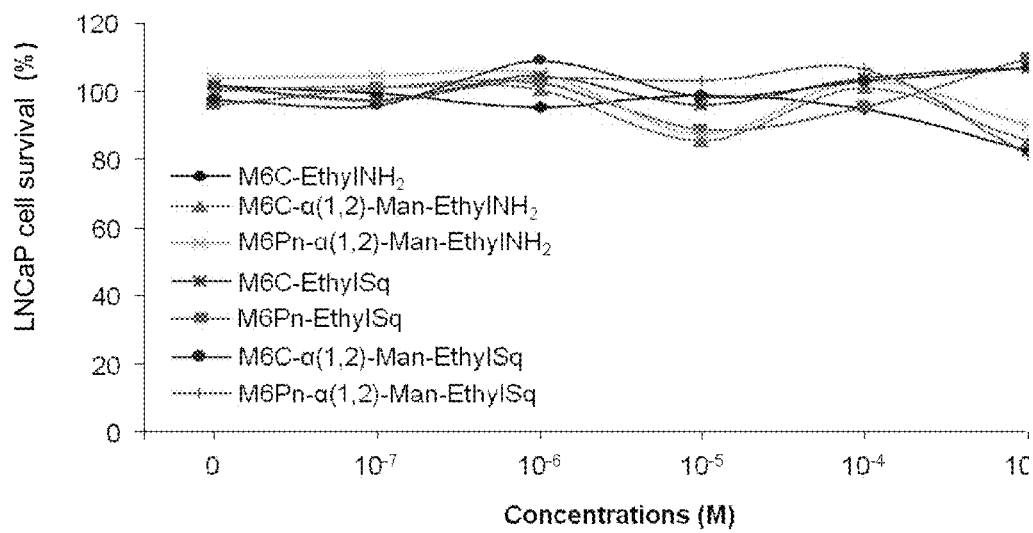

13 Claims, 2 Drawing Sheets
(2 of 2 Drawing Sheet(s) Filed in Color)

(51) Int. Cl.
| | |
|---|---|
| *C07H 15/26* | (2006.01) |
| *A61K 47/69* | (2017.01) |
| *A61K 38/47* | (2006.01) |
| *A61K 41/00* | (2020.01) |
| *A61K 47/26* | (2006.01) |
| *A61K 49/00* | (2006.01) |
| *C12N 9/24* | (2006.01) |
| *C12N 9/96* | (2006.01) |

(52) U.S. Cl.
CPC .......... *A61K 47/26* (2013.01); *A61K 47/6929* (2017.08); *A61K 49/0036* (2013.01); *A61K 49/0093* (2013.01); *C07H 15/18* (2013.01); *C07H 15/26* (2013.01); *C12N 9/2402* (2013.01); *C12N 9/96* (2013.01); *C12Y 302/0102* (2013.01)

(56) References Cited

FOREIGN PATENT DOCUMENTS

| | | |
|---|---|---|
| FR | 3 016 638 | 7/2015 |
| WO | 2011/000958 | 1/2011 |

OTHER PUBLICATIONS

Desnick, et al. "Enzyme Replacement and Enhancement Therapies: Lessons From Lysosomal Disorders" Nature, Dec. 2002, 3:954-966.
Distler, et al. "The Binding Specificity of High and Low Molecular Weight Phosphomannosyl Receptors from Bovine Testes" The Journal of Biological Chemistry, 1991, 266(32):21687-21692.
Hollak, et al. "Treatment of lysosomal storage disorders: successes and challenges" J. Inherit Metab Dis, 2014, 37:587-598.
Jeanjean, et al. "Synthesis and receptor binding affinity of carboxylate analogues of the mannose 6-phosphate recognition marker" Bioorganic and Medicinal Chemistry, 2006, 14:3575-3582.
Jeanjean, et al. "Synthesis of new sulfonate and phosphonate derivatives for cation-independent mannose 6-phosphate receptor targeting" Bioorganic and Medicinal Chemistry Letters, 2008, 18:6240-6243.
Karelin, et al. "Synthesis of Oligosaccharide Fragments of Mannan from Candida albicans Cell Wall and Their BSA Conjugates" Russian Journal of Bioorganic Chemistry, 2007, 33(1):110-121.
Moreland, et al. "Species-specific differences in the processing of acid α-glucosidase are due to the amino acid identity at position 201" Gene, 2012, 491:25-30.
Pereira, et al. "Prediction of the anomeric configuration, type of linkage, and residues in disaccharides from 1D(13)C NMR data" Carbohydrate Research, 2011, 346:960-972.
Pourcelot, et al. "Mantyl tagged oligo alpha (1 -> 2) mannosides as Candida albicans beta-mannosyl transferases substrates: a comparison between synthetic strategies" RSC Advances, 2013, 3(44):22560-22571.
Srivastava, et al. "Synthesis of Phosphorylated Trimannosides Corresponding to End Groups of the High-Mannose Chains of Lysosomal Enzymes" Carbohydrate Research, 1987, 161:195-210.
Tanaka, et al. "Studies directed toward the synthesis of protein-bound GPI anchor" Tetrahedron, 2003, 59:4059-4067.
Van der Ploeg, et al. "Pompe's Disease" Lancet, 2008, 372:1342-1353.
Vidal, et al. "Synthesis and Biological Evaluation of New Mannose 6-Phosphate Analogues" Bioorganic and Medicinal Chemistry, 2002, 10:4051-4056.

MULTI-FUNCTIONALIZED POLYSACCHARIDE COMPOUNDS AND USE THEREOF FOR TARGETING THE CATION-INDEPENDENT MANNOSE 6-PHOSPHATE RECEPTOR

RELATED APPLICATIONS AND INCORPORATION BY REFERENCE

The present patent application is filed pursuant to 35 U.S.C. § 371 as a U.S. National Phase Application of International Patent Application No. PCT/FR2016/052339 filed Sep. 15, 2016, claiming the benefit of priority to French Patent Application No. 15 58806 filed Sep. 18, 2015. The International Application was published as WO 2017/046535 on Mar. 23, 2017. The contents of each of the aforementioned patent applications are herein incorporated by reference in their entirety.

The present invention relates to novel multi-functionalized polysaccharide compounds, and more particularly multi-functionalized di-, tri- or tetramannocide compounds. The invention also relates to the process for preparing said compounds, and to the use thereof for targeting the cation-independent mannose 6-phosphate receptor (CI-M6PR).

The cation-independent mannose 6-phosphate receptor (CI-M6PR) is a ubiquitous receptor which is present both in the cytoplasm and in the membrane of cells. Its main role is to provide the transportation of newly synthesized lysosomal enzymes from the trans-golgi network to the lysosomes where they are active. It also participates in the endocytosis of lysosomal enzymes secreted by the cells. This endocytosis by CI-M6PR allows the internalization of compounds bearing mannose 6-phosphate (M6P) residues into the cell and the trafficking thereof to the lysosomes.

CI-M6PR thus plays a crucial role in the treatment of lysosomal overload diseases (rare disease), and more particularly for enzyme replacement therapy. Enzyme replacement therapy is a therapy used successfully to treat these rare diseases which are characterized by a deficiency of a specific lysosomal enzyme. It consists of the administration of the recombinant lysosomal enzymes which will be directed to the lysosomes via CI-M6PR by virtue of the M6P residues present at the end of their glycosylated chains.

Furthermore, CI-M6PR is overexpressed in certain cancers[1], which makes it an advantageous target for the development of targeted treatments, thus limiting toxicity of healthy cells.

Such therapies can be obtained by the functionalization, for example, of nanoparticles encapsulating an active ingredient and surface-grafted with mannose 6-phosphate (M6P) residues.

However, the major drawback of mannose 6-phosphate (M6P) is the sensitivity of its phosphate function to hydrolysis by the phosphatases present in all the organs and in serum. M6P is then dephosphorylated and is no longer recognized by CI-M6PR. The stability of this recognition marker is therefore a determining element for its use in the transportation of bioactive molecules.

The isosteric analogs of M6P do not have the drawback of degradation by phosphatases[2,3,4]. The ligation of these isosteric analogs of M6P to the oligosaccharide part of lysosomal enzymes makes it possible to improve the efficiency of these enzymes for applications in enzyme replacement therapy[5]. The use of these isosteric analogs also allows very effective targeting of cancer cells of prostate tumors overexpressing CI-M6PR and also their treatment[1].

In order to improve the affinity for CI-M6PR, these same analogs have been synthesized in dimannose series with a glycosidic bond of $\alpha(1,2)$ type. The disaccharide 6-P-Man-$\alpha(1,2)$-Man has an affinity for CI-M6PR which is greater than that of the monosaccharide M6P[6]. The alpha-1,2 linkage between the two mannose residues is very important for obtaining good affinity with respect to CI-M6PR. The alpha-1,3 or alpha-1,4 or alpha-1,6 linkages result in a lower affinity.

The 6-P-Man-$\alpha(1,2)$-Man disaccharide has, however, the drawback of not being stable in the blood. This is because the phosphate function of the 6-P-Man-$\alpha(1,2)$-Man disaccharide undergoes hydrolysis by the phosphatases present in serum. After dephosphorylation by the hydrolases of the serum, the disaccharide formed, Man-$\alpha(1,2)$-Man, is not recognized by CI-M6PR which is the biological target.

There remains at this time the need to find new isosteric analogs of M6P which have an improved affinity for CI-M6PR, and which also are stable in physiological fluids.

One of the objectives of the present invention is therefore to provide novel isosteric analogs of M6P which have a very high affinity for CI-M6PR.

The expression "isosteric analog of M6P" is intended to mean a synthetic chemical compound having the same biological activity as M6P, but improved stability.

Another objective of the invention is to provide novel isosteric analogs of M6P which are stable in physiological fluids.

Another objective of the invention is to provide novel isosteric analogs of M6P which have improved affinity for CI-M6PR compared with the isosteric analogs of M6P that are described in application PCT/EP2010/05950[5].

The inventors have thus imagined novel multi-functionalized di-, tri- or tetramannocide compounds, that is to say compounds that bear various functional groups, said functional groups being capable of forming, respectively, one (or more) bond(s) with CI-M6PR and one (or more) bond(s) with a compound of interest Y.

The difficulty encountered with the compounds provided in the invention is to find an advantageous way to synthesize them, namely in particular a way which is simple to carry out, efficient (good yield) and inexpensive.

Another objective of the invention is therefore to find a process for preparing multi-functionalized di-, tri- or tetramannocide compounds which is advantageous, namely in particular which is simple to carry out, efficient and inexpensive.

Indeed, the synthesis of di-, tri- or tetrasaccharide compounds is more complex to carry out than that of monosaccharide compounds.

A subject of the present invention is a compound characterized in that it has the general formula (I):

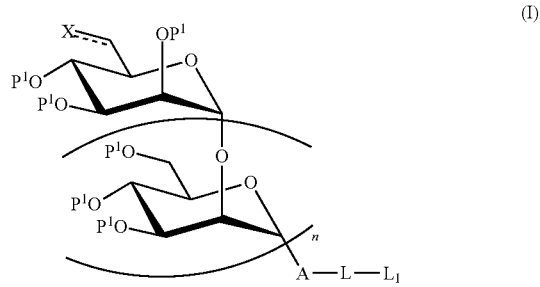

in which:

n is an integer ranging from 1 to 3,

───── represents a single bond or a double bond, each of the P¹ represents, independently of one another, H, or an acid-labile, base-labile, hydrogen-labile, photo-labile, halogen-labile protecting group, in particular chosen from trimethylsilyl (TMS: $(CH_3)_3Si-$), tert-butyldimethylsilyl (TBDMS: $tBuMe_2Si-$), benzyl (Bn: $C_6H_5CH_2$), para-methoxybenzyl (PMB: $4\text{-}CH_3OC_6H_5CH_2-$), ortho-dinitrobenzyl (o-$NO_2C_6H_5CH_2-$), acetyl (Ac: $CH_3CO-$), benzoyl (Bz: $C_6H_5CO-$) or $CF_3CO-$ (trifluoroacetyl), X represents:

when ───── is a single bond:
the phosphonate group:

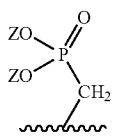

the fluorophosphonate group:

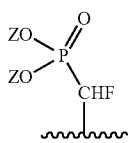

the difluorophosphonate group:

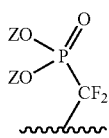

the carboxylate group:

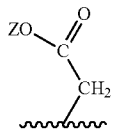

the malonate group:

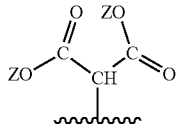

when ───── is a double bond:
the phosphonate group:

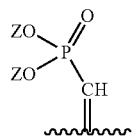

the carboxylate group:

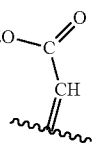

with Z representing, independently of one another, H; a $C_1$-$C_5$ alkyl chosen in particular from methyl (Me: $CH_3-$), ethyl (Et: $C_2H_5$) or isopropyl (iPr: $(CH_3)_3C-$); 2,2,2-trifluoroethyl ($CF_3CH_2-$); $C_6H_5CH_2-$; phenyl (Ph: $C_6H_5-$); $(CH_3)_3Si-$; an alkali metal chosen from Na, Li or K; an ammonium $NH_4$;

A represents a divalent radical chosen from $-O-$, $-S-$, $-NH-$, $-CH_2-$;

L represents:
- $-H$; $-NH_2$; $-(CH_2)_{n1}-CH=CH_2$ or $-(CH_2)_{n1}-C\equiv CH$ with $n_1$ representing an integer ranging from 0 to 4, then in each of these cases, $L_1$ is absent,
- a substituted or unsubstituted, linear or branched, saturated divalent hydrocarbon-based radical having from 1 to 30 carbon atoms, a substituted or unsubstituted, linear or branched, unsaturated divalent hydrocarbon-based radical having from 2 to 30 carbon atoms,
- a saturated or unsaturated divalent hydrocarbon-based radical as defined above, in which one or more $-CH_2-$, $-CH=CH-$ and/or $-C\equiv C-$ groups of the saturated or unsaturated hydrocarbon-based radical is (are) replaced, independently of one another, with an ether ($-O-$) group; amine ($-NH-$) group; alkylamine ($-NR_1-$) group with $R_1$ representing a $C_1$-$C_5$ alkyl; thioether ($-S-$) group; amide ($-CO-NH-$) group; carbamate ($-NH-CO-O-$) group; oxime $-O-N=CH-$ group; acylhydrazone $-CO-NH-N=CH-$ group; a substituted or unsubstituted, saturated or unsaturated, cyclic or heterocyclic system;

$L_1$ represents:
$-(CH_2)_{n1}-CH=CH_2$; $-(CH_2)_{n1}-C\equiv CH$; $-(CH_2)_{n1}-N_3$; $-(CH_2)_{n1}-SH$; $-(CH_2)_{n1}-NH_2$; $-(CH_2)_{n1}-N=C=O$; $-(CH_2)_{n1}-N=C=S$; $-(CH_2)_{n1}-NHR_1$; $-(CH_2)_{n1}-NR_1R_2$; $-(CH_2)_{n1}-A_1-NH_2$; $-(CH_2)_{n1}-A_1-NHR_1$; $-(CH_2)_{n1}-A_1-NR_1R_2$; $-(CH_2)_{n1}-NHCO-CH_2Hal$; $-(CH_2)_{n1}-COZ_1$; $-(CH_2)_{n1}-A_1COZ_1$; $-(CH_2)_{n1}-O-N=CH_2$; $-(CH_2)_{n1}-CO-NH-N=CH_2$; $-(CH_2)_{n1}-H$; a substituted or unsubstituted, saturated or unsaturated, cyclic or heterocyclic system; a halogen chosen from F, Cl, Br or I; with $n_1$ as defined above, $R_1$ and $R_2$ representing, independently of one another, a $C_1$-$C_5$ alkyl, $A_1$ representing $-O-$, $-NH-$, Hal representing Cl, Br or I;

$Z_1$ representing $-OH$, $-OR_1$, $-NH-NH_2$, $-NH-NR_1R_2$, with $R_1$ and $R_2$ as defined above, a halogen chosen from F, Cl, Br or I.

By way of examples of a linear or branched, saturated divalent hydrocarbon-based radical having from 1 to 30 carbon atoms, mention may in particular be made of:

—CH$_2$—CH$_2$—; —CH$_2$—(CH$_2$)$_m$—; —(CH$_2$)$_m$—CH(C$_1$-C$_7$)—(CH$_2$)$_m$—;
—(CH$_2$)$_m$—CH(C$_1$-C$_7$)—(CH$_2$)$_m$—CH(C$_1$-C$_7$)—(CH$_2$)$_m$—; —(CH$_2$)$_m$—C(C$_1$-C$_7$)$_2$—(CH$_2$)$_m$;
—(CH$_2$)$_m$—C(C$_1$-C$_7$)$_2$—(CH$_2$)$_m$—CH(C$_1$-C$_7$)—(CH$_2$)$_m$;
—(CH$_2$)$_m$—C(C$_1$-C$_7$)$_2$—(CH$_2$)$_m$—C(C$_1$-C$_7$)$_2$—(CH$_2$)$_m$—;

with m representing, independently of one another, an integer ranging from 0 to 30 with the condition that the length of the main hydrocarbon-based chain does not exceed 30 carbon atoms, and C$_1$-C$_7$ representing an alkyl having from 1 to 7 carbon atoms. By way of example of C$_1$-C$_7$ alkyl, mention may in particular be made of methyl, ethyl, propyl, isopropyl, butyl, isobutyl, pentyl, hexyl or heptyl.

A linear or branched, unsaturated divalent hydrocarbon-based radical having from 2 to 30 carbon atoms denotes a hydrocarbon-based radical comprising one or more carbon-carbon double bonds and/or one or more carbon-carbon triple bonds. By way of examples of an unsaturated divalent hydrocarbon-based radical, mention may in particular be made of:

—CH═CH—; —(CH$_2$)$_m$—CH═CH—(CH$_2$)$_m$—;
—(CH$_2$)$_m$—CH═CH—(CH$_2$)$_m$—CH═CH—(CH$_2$)$_m$—;
—(CH$_2$)$_m$—CH═CH—CH(C$_1$-C$_7$)—(CH$_2$)$_m$—;
—(CH$_2$)$_m$—CH(C$_1$-C$_7$)—(CH$_2$)$_m$—CH═CH—CH(C$_1$-C$_7$)—(CH$_2$)$_m$—;
—(CH$_2$)$_m$—CH(C$_1$-C$_7$)—CH═CH—(CH$_2$)$_m$—;
—(CH$_2$)$_m$—CH(C$_1$-C$_7$)—CH═CH—(CH$_2$)$_m$—CH═CH—(CH$_2$)$_m$—;
—(CH$_2$)$_m$—CH═CH—C(C$_1$-C$_7$)$_2$—(CH$_2$)$_m$—;
—(CH$_2$)$_m$—CH═CH—C(C$_1$-C$_7$)$_2$—(CH$_2$)$_m$—C(C$_1$-C$_7$)$_2$—(CH$_2$)$_m$—CH═CH;
—(CH$_2$)$_m$—CH═CH—C(C$_1$-C$_7$)$_2$—(CH$_2$)$_m$—CH(C$_1$-C$_7$)—(CH$_2$)$_m$—CH═CH;
—C≡C—; —(CH$_2$)$_m$—C≡C—(CH$_2$)$_m$—; —(CH$_2$)$_m$—C≡C—(CH$_2$)$_m$—C≡C—(CH$_2$)$_m$—;
—(CH$_2$)$_m$—CH═CH—CH(C$_1$-C$_7$)—(CH$_2$)$_m$—C≡C—(CH$_2$)$_m$—CH(C$_1$-C$_7$)—;
—(CH$_2$)$_m$—CH═CH—C(C$_1$-C$_7$)$_2$—(CH$_2$)$_m$—C≡C—(CH$_2$)$_m$—C(C$_1$-C$_7$)$_2$—(CH$_2$)$_m$—;
—(CH$_2$)$_m$—C≡C—CH(C$_1$-C$_7$)—(CH$_2$)$_m$—C≡C—(CH$_2$)$_m$—CH(C$_1$-C$_7$)—(CH$_2$)$_m$;
—(CH$_2$)$_m$—C≡C—C(C$_1$-C$_7$)$_2$—(CH$_2$)$_m$—CH═CH—(CH$_2$)$_m$—CH(C$_1$-C$_7$)—;
—(CH$_2$)$_m$—CH═CH—C(C$_1$-C$_7$)$_2$—(CH$_2$)$_m$—CH(C$_1$-C$_7$)—(CH$_2$)$_m$—C≡C—CH═CH—(CH$_2$)$_m$—;

with m as defined previously.

According to the invention, the term cyclic or heterocyclic "system" denotes, as appropriate, the monovalent or divalent radical originating from a saturated or unsaturated, cyclic or heterocyclic compound, as such.

Thus, when L$_1$ represents a cyclic or heterocyclic system, it will more specifically be a monovalent radical originating from a saturated or unsaturated, cyclic or heterocyclic compound.

When L represents a saturated or unsaturated hydrocarbon-based radical in which one or more —CH$_2$—, —CH═CH— and/or —C≡C— groups is (are) replaced, independently of one another, with a saturated or unsaturated, cyclic or heterocyclic system, then said cyclic or heterocyclic system is a divalent radical originating from a saturated or unsaturated, cyclic or heterocyclic compound.

By way of example of a saturated or unsaturated, cyclic or heterocyclic compound, mention may in particular be made of azetidine, oxetane, thietane, pyrrole, pyranose, furanose, furan, pyrroline, tetra-hydrofuran, thiophene, tetra-hydrothiophene, pyrazole, imidazole, oxazole, isoxazole, pyrazoline, imidazoline, pyrazolidine, imidazolidine, dioxolane, thiazole, isothiazole, thiazolidine, isoxazolidine, triazole, oxadiazole, thiadiazole, thiosuccinimide, tetrazole, pyridine, naphthyridine, phthalimide, pyran, dihydropyran, piperidine, pyridazine, pyridinium, pyrimidine, purine, pyrazine, pteridine, oxazine, dioxine, piperazine, maleimide, morpholine, dioxane, thiazine, thiomorpholine, oxathiane, dithiane, triazine, trioxane, thiadiazine, dithiazine, trithiane, 3-cyclobutene-1,2-dione, cyclobutane, cyclobutene, cyclopentane, cyclopentene, cyclohexane, cyclohexene, cycloheptane, cycloheptene, benzene, toluene, naphthalene, indene, indane, indolizine, indole, benzofuran, indoline, benzothiophene, indazole, benzimidazole, benzthiazole, tetraline, quinoline, chromene, chromane, cinnoline, quinazoline, quinoxaline and phthalazine.

According to the invention, and as previously indicated, said linear or branched, saturated or unsaturated divalent hydrocarbon-based radical, and said saturated or unsaturated, cyclic or heterocyclic system, may also be substituted with one or more substituents chosen from C$_1$-C$_7$ alkyl, C$_2$-C$_7$ alkenyl, and C$_2$-C$_7$ alkynyl, aryl or with functional groups.

By way of example of functional groups, mention may in particular be made of alcohol, amine, amide, ketone, ester, ether, thioether or carboxylic acid functions.

The term "C$_2$-C$_7$ alkenyl" denotes a linear or branched hydrocarbon-based radical having 2 to 7 carbon atoms and comprising one or more carbon-carbon double bonds.

The term "C$_2$-C$_7$ alkynyl" denotes a linear or branched hydrocarbon-based radical having 2 to 7 carbon atoms and comprising one or more carbon-carbon triple bonds.

The term "aryl" denotes a mono-, bi- or tricyclic aromatic hydrocarbon-based system having from 6 to 18 carbon atoms. By way of example, mention may be made of phenyl (C$_6$H$_5$), benzyl (C$_6$H$_5$CH$_2$), phenethyl (C$_6$H$_5$CH$_2$CH$_2$), tolyl (C$_6$H$_4$CH$_3$), xylyl (C$_6$H$_3$(CH$_3$)$_2$), benzylidene (C$_6$H$_5$CH═CH), benzoyl (C$_6$H$_5$CO), biphenyl (or diphenyl) (C$_{12}$H$_9$) or naphthyl (C$_{10}$H$_7$).

According to one embodiment of the invention, in the compound of formula (I) as defined above:

L represents:
—NH$_2$, —(CH$_2$)$_{n1}$—CH═CH$_2$ or —(CH$_2$)$_{n1}$—C≡CH, with n$_1$ as defined above (integer ranging from 0 to 4), then in each of these cases, L$_1$ is absent, a substituted or unsubstituted, linear or branched, saturated divalent hydrocarbon-based radical having from 1 to 10 carbon atoms, a substituted or unsubstituted, linear or branched, unsaturated divalent hydrocarbon-based radical having from 2 to 10 carbon atoms, a saturated or unsaturated, divalent hydrocarbon-based radical as defined above, in which one or more —CH$_2$—, —CH═CH— and/or —C≡C— groups of the saturated or unsaturated hydrocarbon-based radical is (are) replaced, independently of one another, with: an —O— group; —NH— group; —S— group; —CO—NH— group; —NH—CO—O— group; and/or a cyclic or heterocyclic system chosen from:

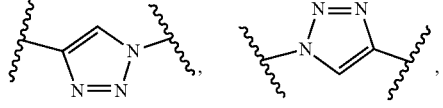

-continued

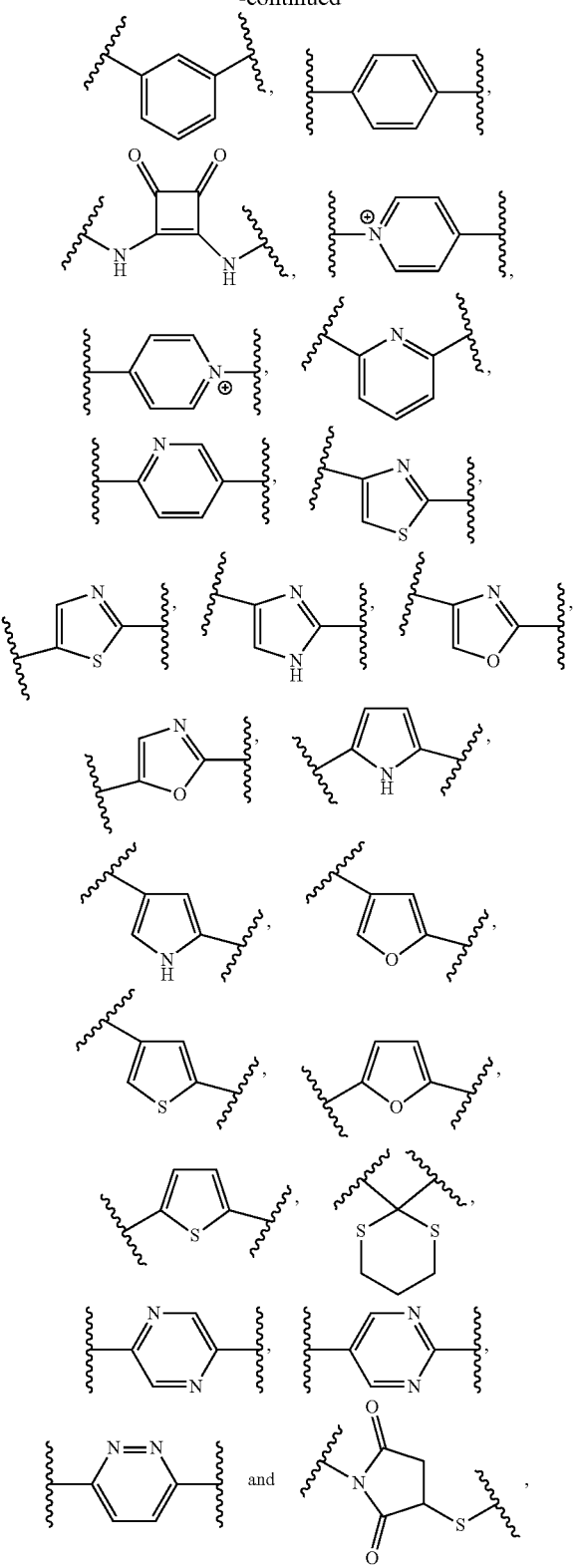

L₁ represents:

—(CH₂)$_{n1}$—CH=CH₂; —(CH₂)$_{n1}$—C≡CH; —(CH₂)$_{n1}$—N₃; —(CH₂)$_{n1}$—SH; —(CH₂)$_{n1}$—NH₂; —(CH₂)$_{n1}$—N=C=O; —(CH₂)$_{n1}$—N=C=S; —(CH₂)$_{n1}$—O—NH₂; —(CH₂)$_{n1}$—NHCO—CH₂Hal; —(CH₂)$_{n1}$—COOH; —(CH₂)$_{n1}$—COOR₁; —(CH₂)$_{n1}$—CO—NH—NH₂; —(CH₂)$_{n1}$—H; a halogen chosen from F, Cl, Br or I;

a cyclic or heterocyclic system chosen from:

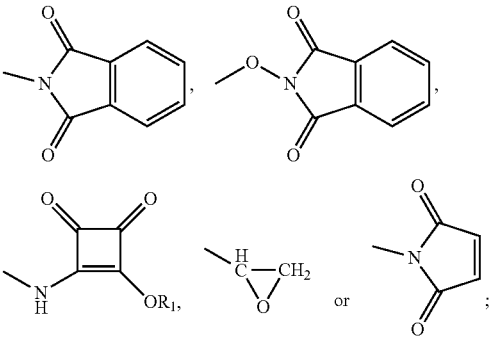

with $n_1$, $R_1$ and Hal as defined above.

By way of examples of compounds of formula (I) as defined above, mention may be made of those for which:

the substituent L is chosen from:

—CH=CH₂, —C≡CH or —NH₂, then in each of these cases, L₁ is absent;

—CH₂—; —CH₂—CH₂—; —(CH₂)₃—; —(CH₂)₄—; —(CH₂)₅—; —CH₂—CH₂—O—CH₂—CH₂—; —(CH₂—CH₂—O)₂—CH₂—CH₂—; —CH₂—CH₂—S—CH₂—CH₂—; —CH₂—CH₂—S—CH₂—CH₂—O—CH₂—CH₂—;

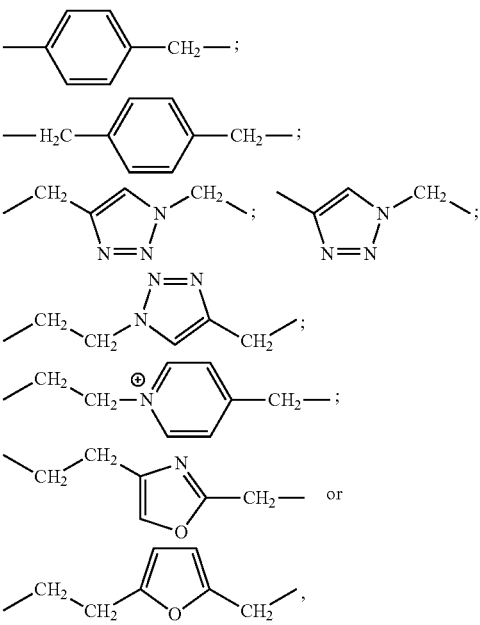

and the substituent L₁ is chosen from:

—CH=CH₂; —C≡CH; —N₃; —SH; —NH₂; —N=C=O; —N=C=S; —O—NH₂; —NHCO—CH₂Cl; —COOH; —COOR₁; —CO—NH—NH₂, a halogen chosen from F, Cl, Br or I, a cyclic or heterocyclic system chosen from:

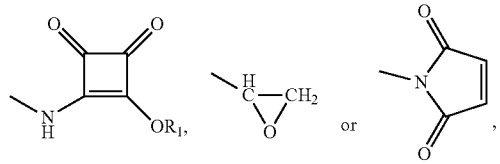

with $R_1$ as defined above.

A compound of formula (I) in which n is equal to 1 is a disaccharide, and more particularly a multi-functionalized di-mannoside corresponding to the formula:

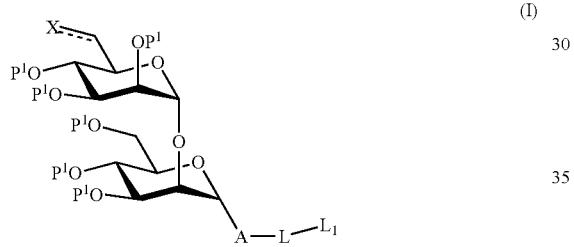
(I)

A compound of formula (I) in which n is equal to 2 is a trisaccharide, and more particularly a multi-functionalized tri-mannoside corresponding to the formula:

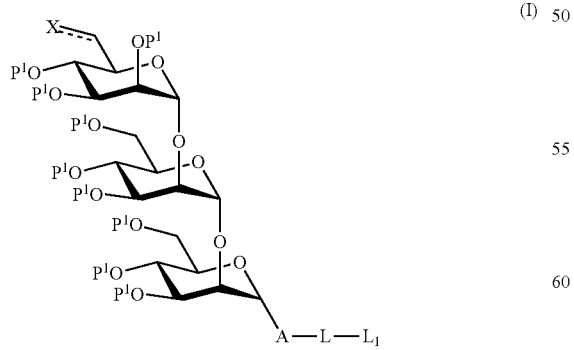
(I)

A compound of formula (I) in which n is equal to 3 is a tetrasaccharide compound, and more particularly a multi-functionalized tetramannoside corresponding to the formula:

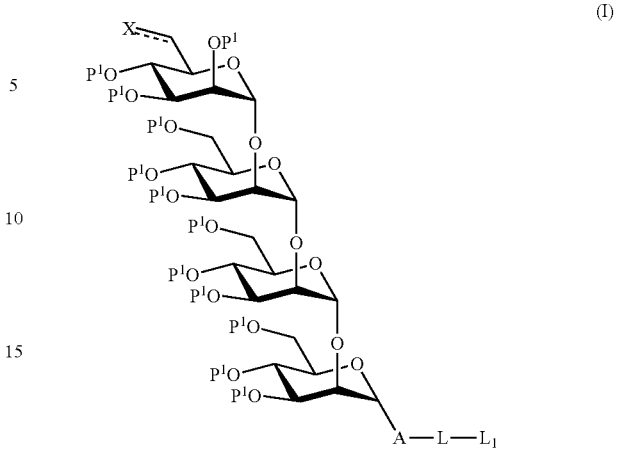
(I)

The invention also relates to a process for preparing a compound of formula (I) as defined above, characterized in that the starting compound used is a compound corresponding to the formula (II):

(II)

in which $P^1$, n, A, L and $L_1$ are as defined above.

These compounds are very advantageous in that they make it possible in particular to prepare compounds of formula (I) in a limited number of steps, and with a good yield.

A subject of the invention is therefore also a compound corresponding to the general formula (II):

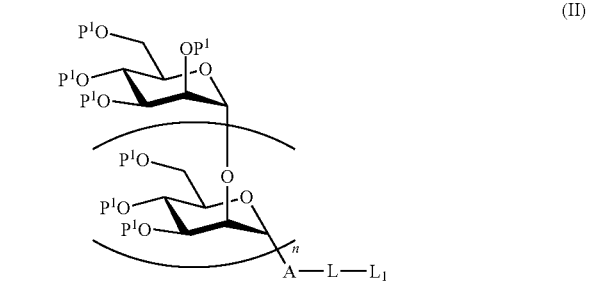
(II)

in which $P^1$, n, A, L and $L_1$ are as defined above.

The preparation of the compound of formula (II) is carried out by reaction between a glycoside acceptor (IV) or (IVa) with a glycoside donor (V), according to one of the reaction schemes below:

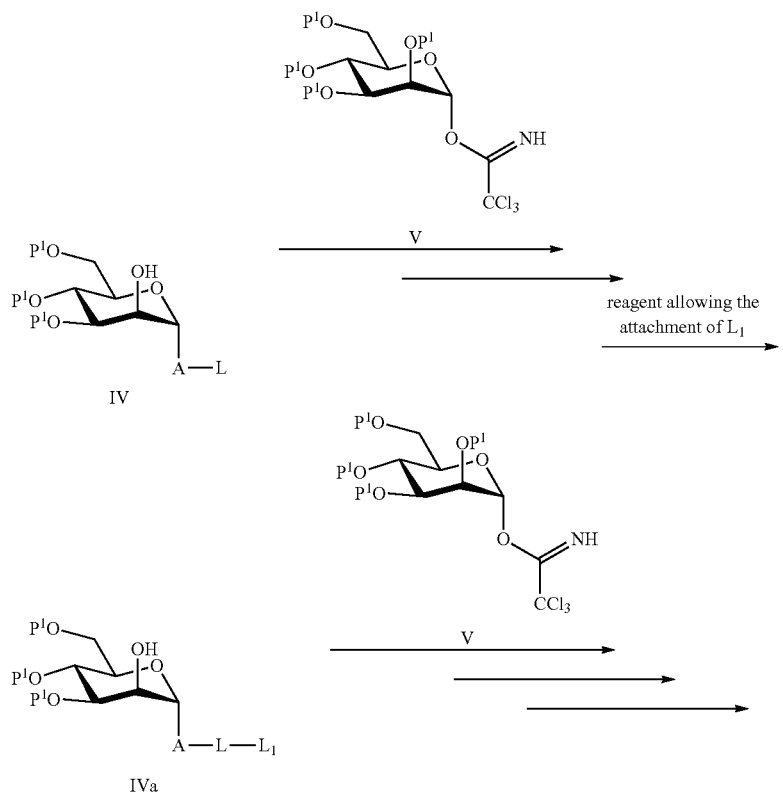
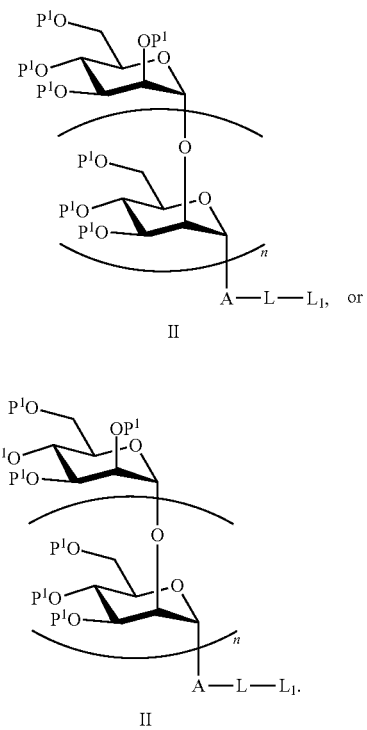

The compounds of the invention of formula (I) are particularly advantageous because, on the one hand, they make it possible to target CI-M6PR with a very high affinity and, on the other hand, they are capable of forming covalent bonds at their group LL₁ with a large number of compounds of interest Ⓨ.

The present invention also relates to a conjugate formed between a compound of interest Ⓨ and the compound of formula (I).

A subject of the invention is thus also a conjugate characterized in that it corresponds to general formula (III):

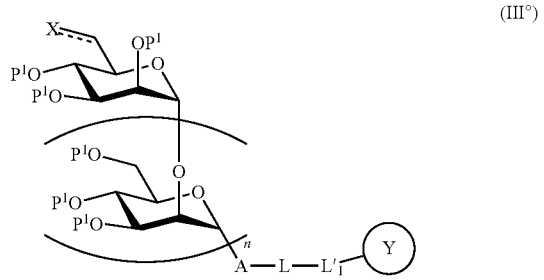

(III°)

in which X, P¹, n, A and L are as defined above,

L'₁ represents the substituent L₁ as defined above involved in a covalent bond with a functional group borne by a compound of interest Ⓨ, said compound of interest Ⓨ being chosen from enzymes, nanoparticles, proteins, antibodies or cytotoxic agents.

According to one embodiment of the invention, the conjugate of formula (III) as defined above has an $IC_{50}$ value for the cation-independent mannose 6-phosphate receptor (CI-M6PR) of at least $10^{-5}$ M, and preferably ranging from $10^{-6}$ to $10^{-9}$ M. The term "$IC_{50}$ value" is intended to mean the concentration of compounds capable of inhibiting the bonding of CI-M6PR to its ligand, pentamannose 6-phosphate (PMP), adsorbed beforehand.

By way of more specific examples of the compound of interest Ⓨ, mention may be made of a lysosomal enzyme or a nanoparticle, in particular a silica nanoparticle.

According to one embodiment of the invention, the nanoparticle may incorporate a photosensibilizer of neutral porphyrin type.

By way of examples of lysosomal enzymes, mention may be made of those chosen from acid alpha-glucosidase, acid beta-galactosidase-1, acid sphingomyelinase, alpha-D-mannosidase, alpha-fucosidase, alpha-galactosidase A, alpha-glucosaminide acetyltransferase, alpha-glucosidase, alpha-L-iduronidase, alpha-N-acetylgalactosaminidase, alpha-acetylglucosaminidase, alpha-D-neuraminidase, arylsulfatase A, arylsulfatase B, beta-galactosidase, beta-glucuronidase, beta-mannosidase, cathepsin D, cathepsin K, ceramidase, cystinosine, ganglioside activator GM2, galactocerebrosidase, glucocerebrosidase, heparan sulfatase, hexosaminidase A, hexosaminidase B, hyaluronidase, iduronate-2-sulfatase, LAMP2, lysosomal acid lipase, N-acetylglucosamine-1-phosphotransferase, N-acetylgalactosamine 6-sulfatase, N-acetylglucosamine-1-phosphotransferase, N-acetylglucosamine-6-sulfate sulfatase, N-aspartyl-beta-glucosaminidase, palmitoyl-thioesterase-1, acid phosphatase, protected protein/cathepsin A (PPCA), sialin, triptidyl-peptidase 1.

Said enzymes are obtained by genetic engineering in production systems which make it possible to obtain biologically active and functional recombinant proteins. For example, for the production of lysosomal glycoproteins, the baculovirus/sf9 insect cells system is used.

The invention also relates to the use of at least one compound of formula (I) as defined above, for forming at least one covalent bond with at least one functional group borne by a compound of interest Ⓨ, said compound of interest Ⓨ being chosen from enzymes, nanoparticles, proteins, antibodies or cytotoxic agents.

According to one advantageous embodiment of the invention, n' compounds of formula (I) can react with n' functional group(s) borne by said compound of interest Y, with n' being an integer ranging from 1 to 1000, and preferably from 1 to 100, so as to form n' covalent bonds.

The invention thus also relates to the use of n' compound(s) of formula (I) for forming n' covalent bond(s) with n' functional group(s) of the compound of interest Ⓨ, with n' as defined above.

A subject of the invention is also the use of n' compound(s) of formula (I) as defined above, for forming the conjugate of general formula (IIIa):

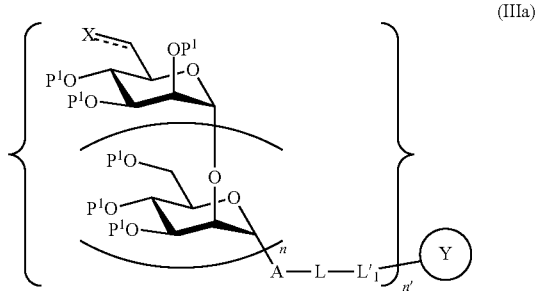

in which $P^1$, X, n, n', A, L, $L'_1$ and Ⓨ are as defined above.

When n' is an integer equal to 1, then the conjugate of general formula (III) and the conjugate of general formula (IIIa) are identical.

The term "conjugate of general formula (III)" refers to a polysaccharide of formula (I) covalently bonded at its $L_1$ group with a functional group of the compound of interest Ⓨ.

The term "conjugate of general formula (IIIa)" refers, when n' is not equal to 1, to at least two polysaccharide(s) of formula (I) covalently bonded with at least two functional groups of the compound of interest Ⓨ.

For example, when the compound of interest Ⓨ is a nanoparticle, the conjugate (IIIa) may comprise 100 polysaccharides of formula (I) forming respectively 100 covalent bonds with 100 functional groups borne by the nanoparticle.

The $LL_1$ group of the compounds (I) of the invention is as defined previously and is capable of binding by covalent bonding, directly or after activation, to at least one of the functions naturally present on or artificially introduced onto the compound of interest Ⓨ.

As previously mentioned through the definition of the substituents L and $L_1$, the substituent $LL_1$ of the compounds (I) of the invention may in particular comprise a reactive group chosen from carboxylic acid and salts thereof, acid chloride, ester (alkyl ester, p-nitrophenyl ester, succinimidyl ester, sulfosuccinimidyl ester, etc.), azido (acyl azide, azidonitrophenyl etc.), hydrazide, 3-acyl-1,3-thiazolidine-2-thione, substituted or unsubstituted amine, O-alkyloxyamine, quaternary ammonium, isocyanate, isothiocyanate, hydrazine, phthalimido, maleimide, haloacetamide, monochlorotriazine, dichlorotriazine, mono- or di-halogenated pyridine, thiol, sulfonyl chloride, vinylsulfone, disulfide, hydroxyl, epoxide or imidazolyl.

In one particular embodiment, the substituent $LL_1$ comprises a reactive carbonyl group chosen from acylhydrazide, hydrazine or O-alkyloxyamine. The reaction between said acylhydrazide, hydrazine or O-alkyloxyamine and a carbonyl group of the compound of interest Ⓨ results respectively in an acylhydrazone bond, a hydrazone bond or an oxime bond. Chemical groups of this type are generally useful for bonding glycoproteins (compound of interest Ⓨ): the carbonyl groups (either naturally present or induced by oxidation of hydroxyl functions of the glycosyl chains of the glycoprotein) available on the fragments of oligosaccharide of the glycoprotein are reacted with the reactive carbonyl groups of the compounds (I) of the invention.

By way of more particular examples:
carbonyl functions of the compound of interest Ⓨ can react with O-alkylamine or acylhydrazide functions of the compound (I) (namely $L_1$=—O—$NH_2$ or —CO—NH—$NH_2$) in order to result in the formation of oxime or acylhydrazone linkages;
amine functions of the compound of interest Ⓨ can react with ethyl squarate or activated ester functions of the compound (I) (namely, for example,

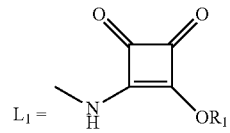

or —COOH activated with N-hydroxysuccinimide (NHS) or with hydroxybenzotriazole (HOBt)) in order to result in the formation of squarate linkages or amide linkages;
thiol functions of the compound of interest Ⓨ can react with thiol, disulfide or maleimide functions of the compound (I) (namely $L_1$=—SH, —S—S—$R_1$ with $R_1$ being $C_1$-$C_5$ alkyl,

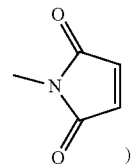

in order to result in the formation of disulfide or thiolene linkages;
alkyne or azide functions of the compound of interest Ⓨ can react respectively with an azide function of the compound (I) (namely $L_1$=$N_3$) or alkyne function (namely $L_1$=—C≡CH) in order to result in the formation of a triazole (which involves a cycloaddition reaction between the azide and the alkyne).

According to the invention, the choice of the substituent $LL_1$ of the compound (I) will depend on the nature of the compound of interest Ⓨ and of the functional groups formed by the latter.

Indeed, those skilled in the art easily understand that the length of the substituent $LL_1$ will increase with the steric hindrance associated with the compound of interest Ⓨ which must be bonded.

For example, if the compound of interest Ⓨ is a protein or glycoprotein, then a substituent $LL_1$ comprising no more than 2 or 3 consecutive atoms will be sufficient to ensure a satisfactory affinity between the compound (I) and CI-M6PR.

On the other hand, if the compound of interest Ⓨ is a protein or a nanoparticle which causes considerable steric hindrance in proximity to the M6P-binding sites of CI-M6PR, then a substituent $LL_1$ comprising more than 2 or 3 consecutive atoms will be required to ensure a satisfactory affinity between the compound (1) and CI-M6PR.

The present invention also relates to a process for preparing a conjugate of formula (III) as defined above or a conjugate of formula (IIIa) as defined above, characterized in that:
- at least one functional group borne by a compound of interest Ⓨ, said compound of interest being as defined above, is reacted with
- at least one compound corresponding to the formula (I):

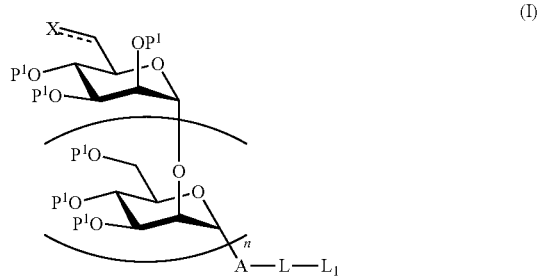

in which $P^1$, X, n, A, L and $L_1$ are as defined above.

According to one embodiment of the invention, a compound of formula (I) as defined above, in which $P^1$ represents a hydrogen, and X, n, A, L and $L_1$ are as defined above, will for example be reacted with at least one functional group borne by the compound of interest Ⓨ as defined above.

Another subject of the invention relates to a conjugate of formula (III) as defined above or a conjugate of formula (IIIa) as defined above:
- for use thereof in a method for therapeutic treatment of the human or animal body, in particular chosen from enzyme replacement therapy, photodynamic therapy or cancer treatment, and/or
- for use thereof in a method of diagnosis, in particular of diagnosis of diseases or ailments associated with an increase or decrease in CI-M6PR expression.

Indeed, by virtue of their high affinity for CI-M6PR, the conjugates (III) and (IIIa) of the invention are particularly useful for the diagnosis of diseases associated with CI-M6PR expression.

When the compound of interest Ⓨ is a nanoparticle incorporating a photosensitizer of porphyrin type, then the conjugate of the invention of formula (III) or (IIIa) will be particularly suitable for photodynamic therapy.

By way of examples of diseases that can be treated using the conjugates (III) or (IIIa) of the invention, mention may be made of diseases caused by a deficiency of the compound of interest Ⓨ in the lysosome. This deficiency may be compensated for by the administration of the conjugate of the invention, which is capable of specifically delivering to the lysosome the compound of interest Ⓨ that is deficient.

BRIEF DESCRIPTION TO THE DRAWINGS

The patent or application file contains at least one drawing executed in color. Copies of this patent or patent application publication with color drawings will be provided by the Office upon request and payment of the necessary fee.

Figure 2:
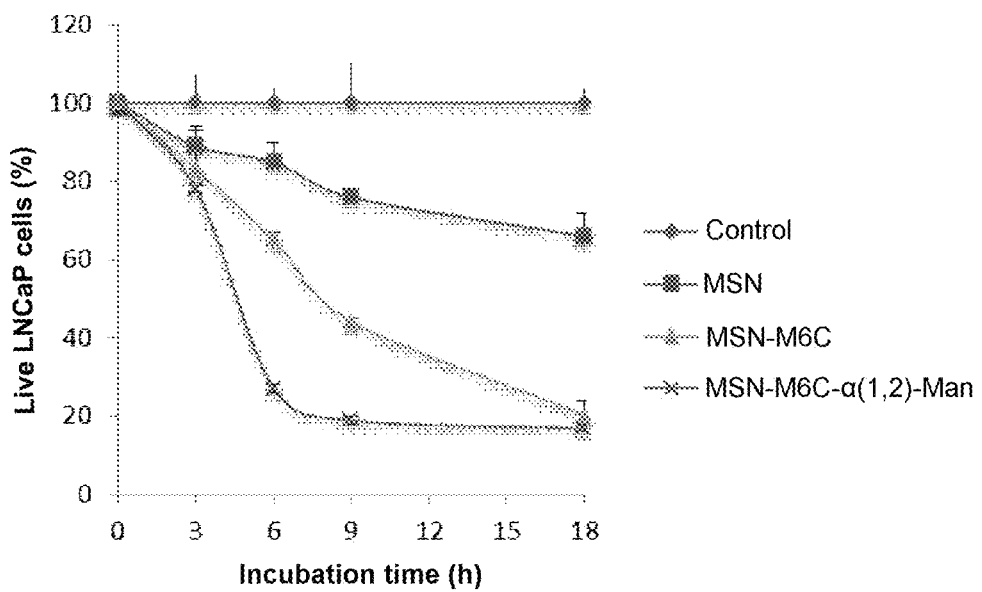

The invention will be understood more clearly on reading the following nonlimiting and purely illustrative examples, and the following FIGS. 1 and 2.

FIG. 1 is a comparison of the cytotoxicity of the phosphonate disaccharides 18, 19 (i.e. M6Pn-α(1,2)-Man-Ethyl-$NH_2$ and M6Pn-α(1,2)-Man-EthylSq) and carboxylate disaccharides 24 and 25 (i.e. M6C-α(1,2)-Man-Ethyl-$NH_2$ and M6C-α(1,2)-Man-EthylSq) of formula (I) of the invention on LNCaP cells and of their respective monosaccharide homologs.

FIG. 2 represents the phototoxic effects, on LNCaP cells, of silica nanoparticles alone (MSN) and of silica nanoparticles (MSN) grafted onto monosaccharide carboxylate analogs (M6C-EthylSq) and disaccharide carboxylate analogs 25 (M6C-α(1,2)-Man-EthylSq) at various incubation times. The nanoparticles grafted onto the monosaccharide carboxylate analog and onto the disaccharide carboxylate analog are represented respectively by "MSN-M6C-EthylSq" and "MSN-M6C-α(1,2)-Man-EthylSq".

Figure 3:
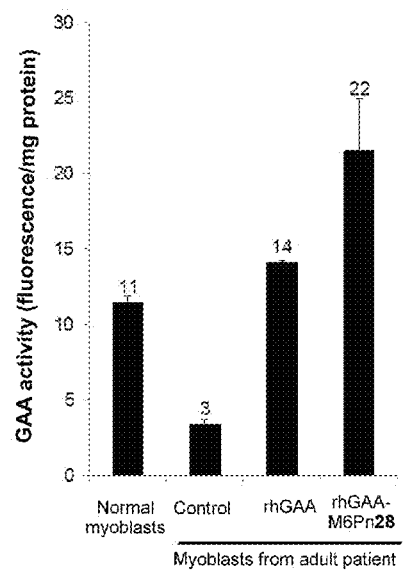

FIG. 3 indicates the assaying of the GAA catalytic activity in myoblasts of patients suffering from the adult form of Pompe disease after incubation for 48 h in the presence of 50 nM rhGAA or of the conjugate of formula (III) of the invention, namely the rhGAA-M6Pn-α(1,2)-Man-Ethyloxyamino conjugate (28) (called rhGAA-M6Pn28 in FIG. 3).

Figure 4:
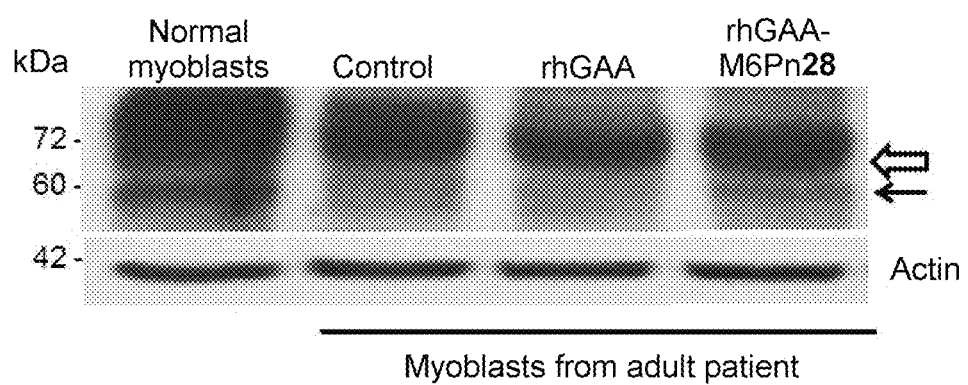

FIG. 4 presents the analysis of the amounts of mature GAA by Western blot with an anti-human GAA antibody (anti-LYAG, Genetex) or an anti-human actin antibody (Invitrogen) after incubation of the myoblasts for 48 h in the presence of 50 nM rhGAA or of the conjugate of formula (III) of the invention, namely the rhGAA-M6Pn-α(1,2)-Man-Ethyloxyamino conjugate (28) (called rhGAA-M6Pn28 in FIG. 4).

EXAMPLE 1

Synthesis of Compounds of Formula (I)

This example describes the preparation of multi-functionalized disaccharides corresponding to the formula (I) in which n is an integer equal to 1; $P^1$ represents, independently of one another, H, $(CH_3)_3Si$— or $C_6H_5CH_2$—; ===== represents a single or double bond; X represents the phosphonate group or the carboxylate group with Z representing, independently of one another, H, ethyl or Na; A represents oxygen; L represents —$CH_2$—$CH_2$—; $L_1$ represents —Br, —$NH_2$, —$N_3$,

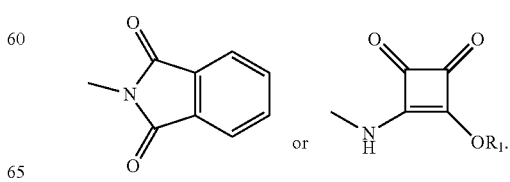

or

1) Preparation of Disaccharides 9, 10, 11 and 12 Corresponding to the Formula (II)

a) Preparation of a Saccharide Acceptor 6: 3,4,6-tri-O-benzyl-α-D-mannopyranoside of 2-bromoethyl 5

The process of preparing a saccharide acceptor 6 corresponding to the general formula (IVa), in which $P^1$ represents Bn, A represents O, L represents $CH_2$—$CH_2$ and $L_1$ represents Br, is illustrated below:

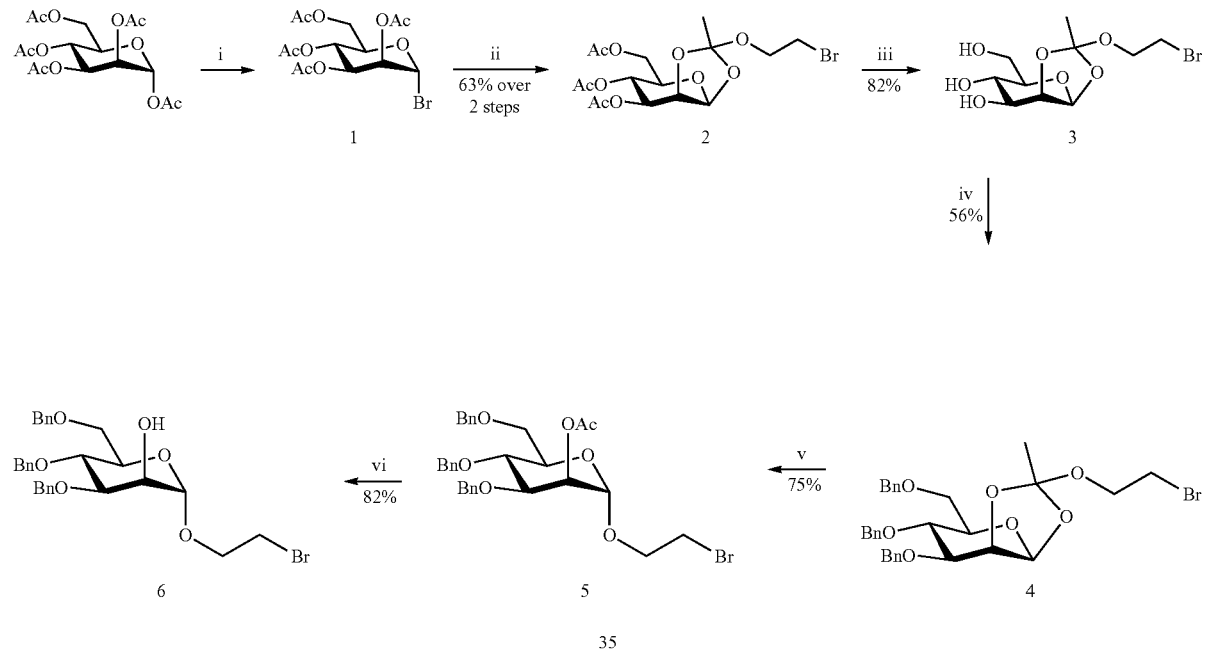

The starting compound is pentaacetylated α-D-mannose onto which a bromine is introduced in the anomeric position using 33% hydrobromic acid in acetic acid, so as to form the compound 1. The intermediate 1 is then reacted with 2-bromoethanol and 2,6-lutidine so as to form the orthoester 2 with a yield of 63% over two steps. The acetates present on positions 3, 4 and 6 of the orthoester 2 are then saponified so as to give the intermediate 3 with a yield of 82%. This deprotection step is total and does not require purification. These same positions 3, 4 and 6 are then benzylated through the action of benzyl bromide so as to form the compound 4 with a yield of 56%. The orthoester 4 is then opened in the presence of $BF_3.Et_2O$ and 2-bromoethanol so as to form the key intermediate 5 with a yield of 75%. The compound 5 is thus functionalized in the anomeric position and bears a protecting group in position 2 orthogonal to the groups of positions 3, 4 and 6. It is thus possible to selectively deprotect this position 2 using a sodium oxide solution so as to obtain the intermediate 6 with a yield of 82%.

The saccharide acceptor 6 is functionalized in the anomeric position: the synthon 6 will therefore be common regardless of the desired disaccharide of formula (II).

Conditions and reagents: (i) 33% HBr, AcOH, AT, 1 h; (ii) 2-bromoethanol, 2,6-lutidine, DCM, 40° C., 3 h; (iii) 1N NaOH, THF, AT, 16 h; (iv) BnBr, NaH, DMF, AT, 21 h; (v) 2-bromoethanol, $BF_3.Et_2O$, AT, 1 h30; (vi) 1N NaOH, THF, AT, 21 h.

Experimental Section

Preparation of 1-bromo-2,3,4,6-tetra-Oacetyl-α-D-mannopyranose 1

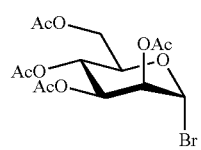

1

10 g of α-D-mannose pentaacetate are dissolved in 20 ml of a solution of hydrobromic acid at 33% in acetic acid. The yellow solution is stirred for 1 h at ambient temperature. The reaction mixture is cooled to 0° C., diluted with 30 ml of $CH_2Cl_2$ and neutralized using a saturated solution of $NaHCO_3$. The aqueous phase is extracted with $CH_2Cl_2$ (5×100 ml). The organic phases are combined, dried over $MgSO_4$ and concentrated so as to give the compound 1 (11.9 g) which is used for the next step without purification.

$C_{14}H_{19}BrO_9$   Chemical formula 1:

Exact weight: 410.02 g·mol$^{-1}$ $R_f$: 0.76 [EtOAc/Cyclo (1:1)]

Preparation of 1,2-O-(1-(2-bromoethoxy)ethyl-idene)-3,4,6-tri-O-acetyl-α-D-mannopyranose 2

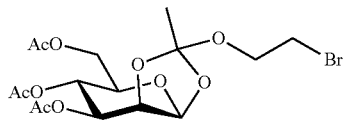

2

11.08 g (1 eq; 26.9 mmol) of compound 1 are dissolved in 9.5 ml of $CH_2Cl_2$ and 9.4 ml (3 eq; 80.7 mmol) of 2,6-lutidine. 4.8 ml (2.5 eq; 67.25 mmol) of 2-bromoethanol are added. The orange-colored reaction medium is heated to 40° C. and stirred for 4 h. A white precipitate is formed. The solution is cooled to ambient temperature and 12 ml of $Et_2O$ are added. The precipitate is filtered off. The filtrate is diluted with 30 ml of $CH_2Cl_2$ and washed successively with 30 ml of water, 30 ml of a saturated solution of $NaHCO_3$ and 30 ml of brine. The combined aqueous phases are extracted with 50 ml of $CH_2Cl_2$. The organic phases are combined and then dried over $MgSO_4$ and concentrated. The residue obtained is dissolved in 20 ml of $CH_2Cl_2$ and 25 ml of ethanol are added. The solution is cooled to −30° C. so as to give the compound 2 in the form of white crystals with a yield of 51% (6.268 g; 13.8 mmol) over two steps.

$C_{16}H_{23}BrO_{10}$     Chemical formula 2:

Exact weight: 454.05 g·mol$^{-1}$
$R_f$: 0.49 [Cyclo/EtOAc (1:1)]
MS, ESI$^+$ m/z: 477 [M+Na]$^+$ Preparation of 1,2-O-(1-(2-bromoethoxy)ethylidene-α-D-mannopyranose 3

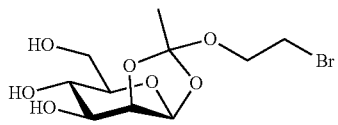

3

4.79 g (1 eq; 10.6 mmol) of compound 2 are dissolved in 22 ml of THF. 43 ml of a 1N aqueous NaOH solution are added. The solution becomes cloudy. 2 ml of methanol are added and the solution becomes clear. The reaction mixture is stirred at ambient temperature for 16 h. 250 ml of ethyl acetate are added and the aqueous phase is extracted with 3×200 ml of ethyl acetate. The organic phases are combined and then dried over $MgSO_4$ and concentrated. The residue obtained is purified by automated flash chromatography on silica gel ($CH_2Cl_2$/MeOH: from 0 to 5% in 15 min; 5% for 10 min; from 5 to 10% in 15 min) so as to give the compound 3 in the form of a colorless oil with a yield of 82% (2.86 g; 8.69 mmol).

$C_{10}H_{17}BrO_7$     Chemical formula 3:

Exact weight: 328.02 g·mol$^{-1}$
$R_f$: 0.36 [$CH_2Cl_2$/MeOH (9:1)]
MS, ESI$^-$ m/z: 373 [M−H+HCOOH]$^-$ Preparation of 1,2-O-(1-(2-bromoethoxy)ethylidene-3,4,6-tri-O-benzyl-α-D-mannopyranose 4

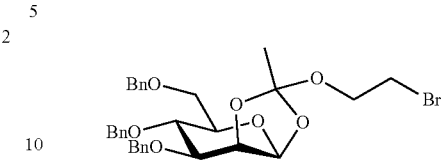

4

2.86 g (1 eq; 8.69 mmol) of the compound 3 are dissolved in 40 ml of DMF. 4.2 ml (4 eq; 34.76 mmol) of benzyl bromide are added. The reaction mixture is cooled to 0° C. and 874 mg (3 eq; 26 mmol) of a 60% dispersion of NaH in oil are added. After stirring for 17 h30 at ambient temperature, partially benzylated product remains. The addition of one equivalent of benzyl bromide and of NaH does not cause the reaction to progress. 50 ml of $Et_2O$ and 40 ml of water are added. The aqueous phase is extracted with 2×100 ml of $Et_2O$. The organic phases are combined, washed with 5×80 ml of water and then dried over $MgSO_4$ and concentrated. The residue obtained is purified by automated flash chromatography on silica gel (cyclohexane/$Et_2O$: from 0 to 10% in 15 min; 10% for 10 min; from 10 to 20% in 15 min; 20% for 50 min; from 20 to 40% in 30 min) so as to give the compound 4 in the form of a white solid with a yield of 56% (2.92 g; 4.87 mmol).

$C_{31}H_{35}BrO_7$     Chemical formula 4:

Exact weight: 598.16 g·mol$^{-1}$
$R_f$: 0.43 [Cyclo/$Et_2O$ (1:1)]
MS, ESI$^+$ m/z: 621 [M+Na]$^+$ Preparation of 2-bromoethyl 2-O-acetyl-3,4,6-tri-O-benzyl-α-D-mannopyranoside 5

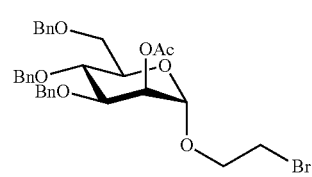

5

1 g (1 eq; 1.67 mmol) of the compound 4 is dissolved of 20 ml of $CH_2Cl_2$. 236 µl (2 eq; 3.34 mmol) of 2-bromoethanol are added and the reaction mixture is stirred at ambient temperature for 10 min. 211 µl (1 eq; 1.67 mmol) of $BF_3.Et_2O$. The reaction mixture is stirred at ambient temperature for 16 h. The solution became pale yellow. The reaction is diluted with 50 ml of saturated solution of $NaHCO_3$. The aqueous phase is extracted with 3×50 ml of $CH_2Cl_2$. The organic phases are combined, washed with 100 ml of brine and then dried over $MgSO_4$ and concentrated. The residue obtained is purified by automated flash chromatography on silica gel (cyclohexane/$Et_2O$: 0 to 30% in 30 min; 30% for 20 min) so as to give the compound 5 in the form of a colorless oil with a yield of 75% (750 mg; 1.25 mmol).

$C_{31}H_{35}BrO_7$     Chemical formula 5:

Exact weight: 598.16 g·mol$^{-1}$
$R_f$: 0.45 [Cyclo/$Et_2O$ (1:1)]
MS, ESI$^+$ m/z: 621 [M+Na]$^+$ Preparation of 2-bromoethyl 3,4,6-tri-O-benzyl-α-D-mannopyranoside 6

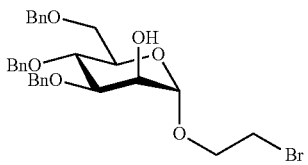

750 mg (1 eq; 1.25 mmol) of the compound 5 are dissolved in 1.6 ml of THF. 2.5 ml (2 eq; 2.5 mmol) of a 1N NaOH solution are added. The solution becomes cloudy. The solution is stirred at ambient temperature for 21 h. The solution is neutralized with a 1N HCl solution. 40 ml of $CH_2Cl_2$ are added. The aqueous phase is extracted with 3×40 ml of $CH_2Cl_2$. The organic phases are combined and then dried over $MgSO_4$ and concentrated. The residue obtained is purified by automated flash chromatography on silica gel (cyclohexane/$Et_2O$: from 0 to 20% in 15 min; 20% for 10 min; from 20 to 30% in 15 min; 30% for 15 min) so as to give the compound 6 in the form of a colorless oil with a yield of 82% (575 mg; 1.03 mmol).

$C_{29}H_{33}BrO_6$　　　　　　Chemical formula 6:

Exact weight: 556.16 g·mol$^{-1}$
$R_f$: 0.29 [Cyclo/$Et_2O$ (7:3)]
MS, ESI$^+$ m/z: 579 [M+Na]$^+$ b) Preparation of a Saccharide Donor 8: 2,3,4,6-tetra-O-acetyl-α-D-mannopyranose trichloroacetimidate The process for preparing a saccharide donor compound 8 corresponding to the general formula (V), in which $P^1$ represents Ac, is illustrated below:

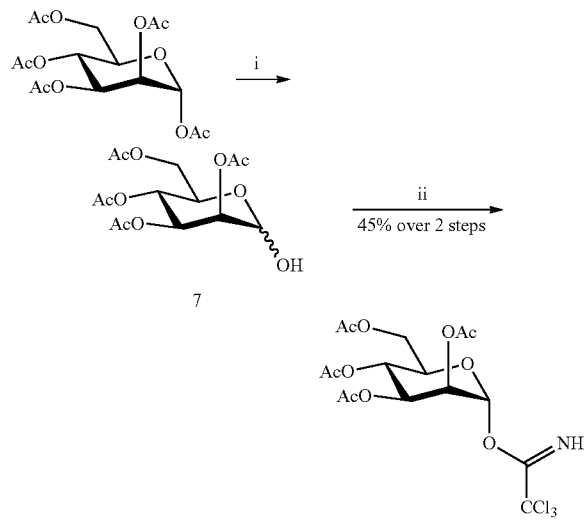

The starting compound is pentaacetylated α-D-mannose which is deprotected in the anomeric position using mor-pholine so as to give the compound 7 without purification. The trichloroacetimidate 8 is then formed by reacting the compound 7 with trichloroacetonitrile in the presence of DBU.

Conditions and reagents: (i) morpholine, DCM, reflux, 3 h30; (ii) $Cl_3CCN$, DBU, DCM, AT, 4 h.

Experimental Section

Preparation of 2,3,4,6-tetra-O-acetyl-D-mannose 7

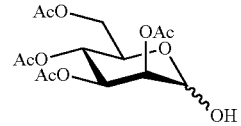

3 g (1 eq; 7.69 mmol) of α-D-mannose pentaacetate are dissolved in 18 ml of $CH_2Cl_2$. 2.7 ml (4 eq; 30.76 mmol) of morpholine are added. The reaction mixture is refluxed for 3 h30 and then cooled to ambient temperature. The solution is neutralized with a 1N HCl solution. The organic phase is washed with 3×10 ml of water, dried over $MgSO_4$ and concentrated so as give the product 7 in the form of a yellow oil that is directly used for the next step.

$C_{14}H_{20}O_{10}$　　　　　　Chemical formula 7:

Exact weight: 348.30 g·mol$^{-1}$
$R_f$: 0.38 [Cyclo/EtOAc (1:1)]
MS, ESI$^-$ m/z: 393 [M−H+HCOOH]$^-$ Preparation of trichloroacetimidate 2,3,4,6-tetra-O-acetyl-α-D-mannopyranose 8

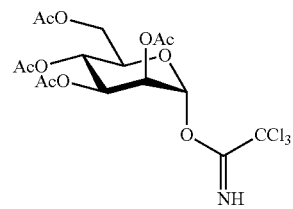

1.34 g (1 eq; 3.85 mmol) of the compound 7 are dissolved in 8.6 ml of $CH_2Cl_2$. The yellow-colored solution is cooled to 0° C. 2.7 ml (7 eq; 26.95 mmol) of trichloroacetonitrile and 575 μl of DBU (1.8-diazabicyclo[5.5.0]undec-7-ene) are added. The solution becomes brown. The reaction medium is stirred for 4 h at ambient temperature and then concentrated. The residue obtained is purified by automated flash chromatography on silica gel (cyclohexane/$Et_2O$: 50% for 25 min) so as to give the compound 8 in the form of a pale yellow oil with a yield of 45% (860 mg; 1.75 mmol). The relatively unstable product is rapidly used.

$C_{16}H_{20}Cl_3NO_{10}$　　　　　　Chemical formula 8:

Exact weight: 492.69 g·mol$^{-1}$
$R_f$: 0.4 [Cyclo/$Et_2O$ (3:7)]

c) Preparation of the Disaccharides 9, 10, 11 and 12

The process for preparing disaccharides 9, 10, 11 and 12 corresponding to the formula (II) is illustrated below:

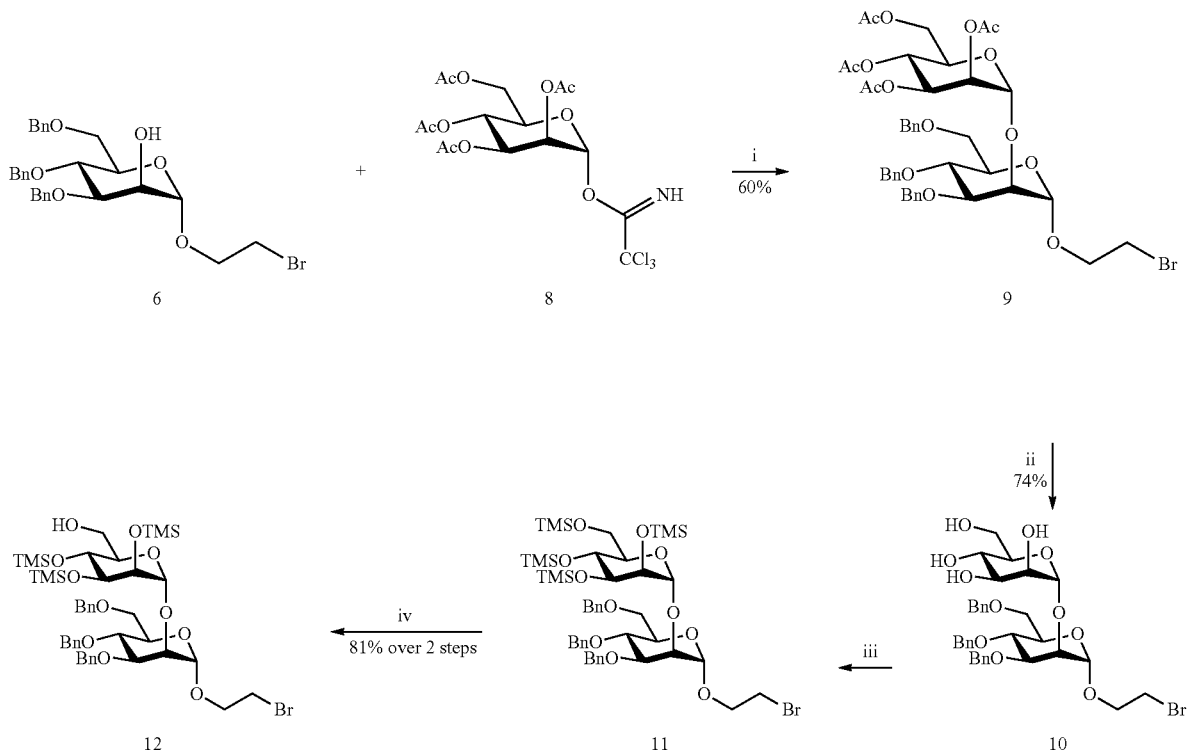

The glycosylation reaction between the acceptor of formula IV or IVa, in particular the saccharide 6, and the donor of formula V, in particular the saccharide 8, makes it possible to obtain the compound of formula (II), in particular the disaccharide 12, which occupies a central position in the synthesis strategy of the invention. This is because the compound of formula (II) makes it possible to diverge toward all of the compounds of formula (I) of the invention. The isosteric analogs of M6P of the invention (I) are in fact accessible starting from the compound of formula (II).

The synthesis process of the invention imparts flexibility in the production of the disaccharide analogs of formula (I) of the invention, but also to the tri- or tetrasaccharide analogs of formula (I) of the invention.

The respective "saccharide acceptor" 6 and "saccharide donor" 8 compounds as prepared above are reacted in the presence of trimethylsilyl triflate so as to form the disaccharide 9 with a yield of 60%. The acetate groups are then saponified so as to give the compound 10 with a yield of 74%. The alcohols thus being protected are then trimethylsilylated through the action of trimethylsilyl chloride so as to form the intermediate 11. Position 6 is then selectively desilylated in the presence of potassium carbonate in methanol so as to give the disaccharide 12 with a yield of 81% over two steps.

Conditions and reagents: (i) TMSOTf, DCM, −30° C., 30 min; (ii) 1N NaOH, THF, AT, 18 h; (iii) TMSCl, NEt$_3$, DCM, AT, 18 h; (iv) K$_2$CO$_3$, MeOH, AT, 1 h45.

Experimental Section

Preparation of bromoethyl 2,3,4,6-tetra-O-acetyl-α-D-mannopyranosyl-(1→2)-3,4,6-tri-O-benzyl-α-D-mannopyranoside 9

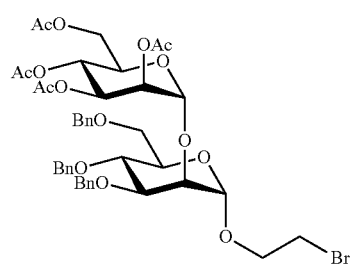

430 mg (1 eq; 0.77 mmol) of the compound 6 and 860 mg (2.27 eq; 1.75 mmol) of the compound 8 are dissolved in 15 ml of CH$_2$Cl$_2$ in the presence of 7 g of pre-activated molecular sieve 4 Å. The reaction medium is stirred for 30 min at ambient temperature and then cooled to −30° C. 167 µl (1.2 eq; 0.924 mmol) of TMSOTf are added dropwise. The reaction mixture is stirred at −30° C. for 1 h15. The reaction medium is then neutralized with 3.5 ml of pyridine. After filtration through celite, the filtrate is concentrated and then co-evaporated with toluene. The residue (pale yellow solid) is purified by automated flash chromatography on silica gel (cyclohexane/Et$_2$O: 30% for 110 min) so as to give the product 9 in the form of a colorless oil with a yield of 64% (441 mg; 0.497 mmol).

$C_{43}H_{51}BrO_{15}$      Chemical formula 9:

Exact weight: 886.24 g·mol$^{-1}$ $R_f$: 0.56 [Cyclo/Et$_2$O (2:8)]

MS, ESI$^+$ m/z: 909 [M+Na]$^+$

Preparation of bromoethyl α-D-mannopyranosyl-(1→2)-3,4,6-tri-O-benzyl-α-D-mannopyranoside 10

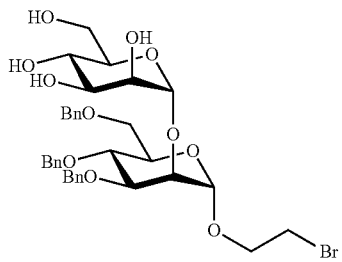

10

5.84 g (1 eq, 6.58 mmol) of the compound 9 are dissolved in 16 ml of THF. 33 ml (5 eq, 32.9 mmol) of a 1 M sodium hydroxide solution are added. The solution becomes cloudy. 1.5 ml of methanol are added. The solution is stirred at ambient temperature for 18 h and then neutralized with a 1M HCl solution and concentrated. The residue obtained is purified by flash chromatography on silica gel (DCM/MeOH: 0% (500 ml); 5% (500 ml); 7% (500 ml); 10% (1 L)) so as to give the compound 10 in a form of a white foam with a yield of 74% (3.5 g, 4.86 mmol).

$C_{35}H_{43}BrO_{11}$  Chemical formula 10:

Molar mass: 718.2 g·mol$^{-1}$
$R_f$: 0.41 [DCM/MeOH (9:1)]

Preparation of bromoethyl 2,3,4,6-tetra-O-trimethylsilyl-α-D-mannopyranosyl-(1→2)-3,4,6-tri-O-benzyl-α-D-mannopyranoside 11

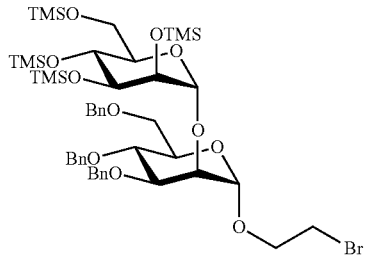

11

3.4 g (1 eq, 4.72 mmol) of the compound 10 are dissolved in 24 ml of freshly distilled DCM and 19 ml (30 eq; 141.6 mmol) of triethylamine. The solution is cooled to 0° C. and 4.8 ml (8 eq; 37.8 mmol) of trimethylsilyl chloride are added dropwise. After stirring for 18 h at ambient temperature, a small amount of starting product remains. 1.2 ml (2 eq; 9.44 mmol) of trimethylsilyl chloride are added dropwise. After stirring for 1 h30 at ambient temperature, there is no progression. The solution is concentrated. The pink residue is dissolved in cyclohexane and filtered through celite. The filtrate is concentrated so as to obtain the compound 11 in the form of a light brown oil that is directly used for the next step.

$C_{47}H_{75}BrO_{11}Si_4$  Chemical formula 11:

Molar mass: 1008.34 g·mol$^{-1}$
$R_f$: 0.78 [Cyclo/Et$_2$O (7:3)]

Preparation of bromoethyl 2,3,4-tri-O-trimethylsilyl-α-D-mannopyranosyl-(1→2)-3,4,6-tri-O-benzyl-α-D-mannopyranoside 12

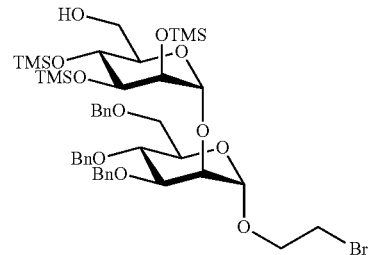

12

4.58 g (4.72 mmol; 1 eq) of the compound 11 are dissolved in 65 ml of freshly distilled methanol. A solution of 6.5 mg (0.01 eq; 0.0472 mmol) of K$_2$CO$_3$ (final concentration=0.63 mM) in 10 ml of methanol is added dropwise. The reaction medium is stirred for 1 h45 at ambient temperature and then diluted with 200 ml of CH$_2$Cl$_2$ and washed with 125 ml of brine. The aqueous phase is extracted with 260 ml of CH$_2$Cl$_2$. The organic phases are combined, dried over MgSO$_4$ and concentrated. The residue obtained (light brown oil) is purified by chromatography on silica gel (Cyclohexane/Et$_2$O: 30% (700 ml); 40% (500 ml); 50% (500 ml); 70% (500 ml)) so as to give the compound 12 (3.58 g; 3.82 mmol) in the form of a colorless liquid with a yield of 81% over two steps.

$C_{44}H_{67}BrO_{11}Si_3$  Chemical formula 12:

Molar mass: 936.16 g·mol$^{-1}$
$R_f$: 0.45 [Cyclo/Et$_2$O (1:1)]
MS, ESI$^+$ m/z: 959 [M+Na]$^+$ 2) Preparation of Disaccharides 14, 15, 16, 17, 18 and 19 Corresponding to the Formula (I) in which X Represents the Phosphonate Group The process for preparing disaccharides 14, 15, 16, 17, 18 and 19 corresponding to the formula (I) in which X represents the phosphonate group is illustrated below:

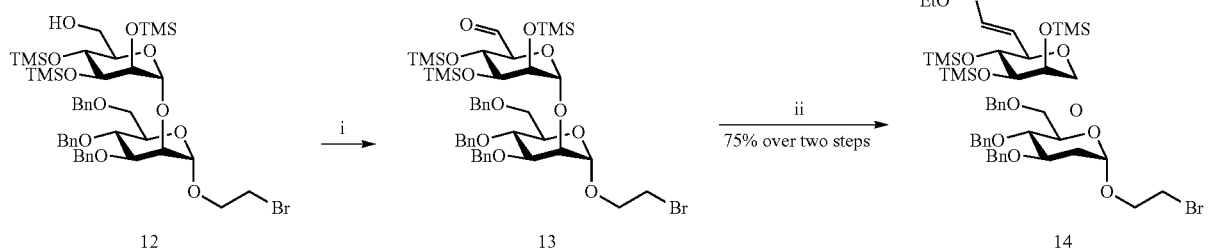

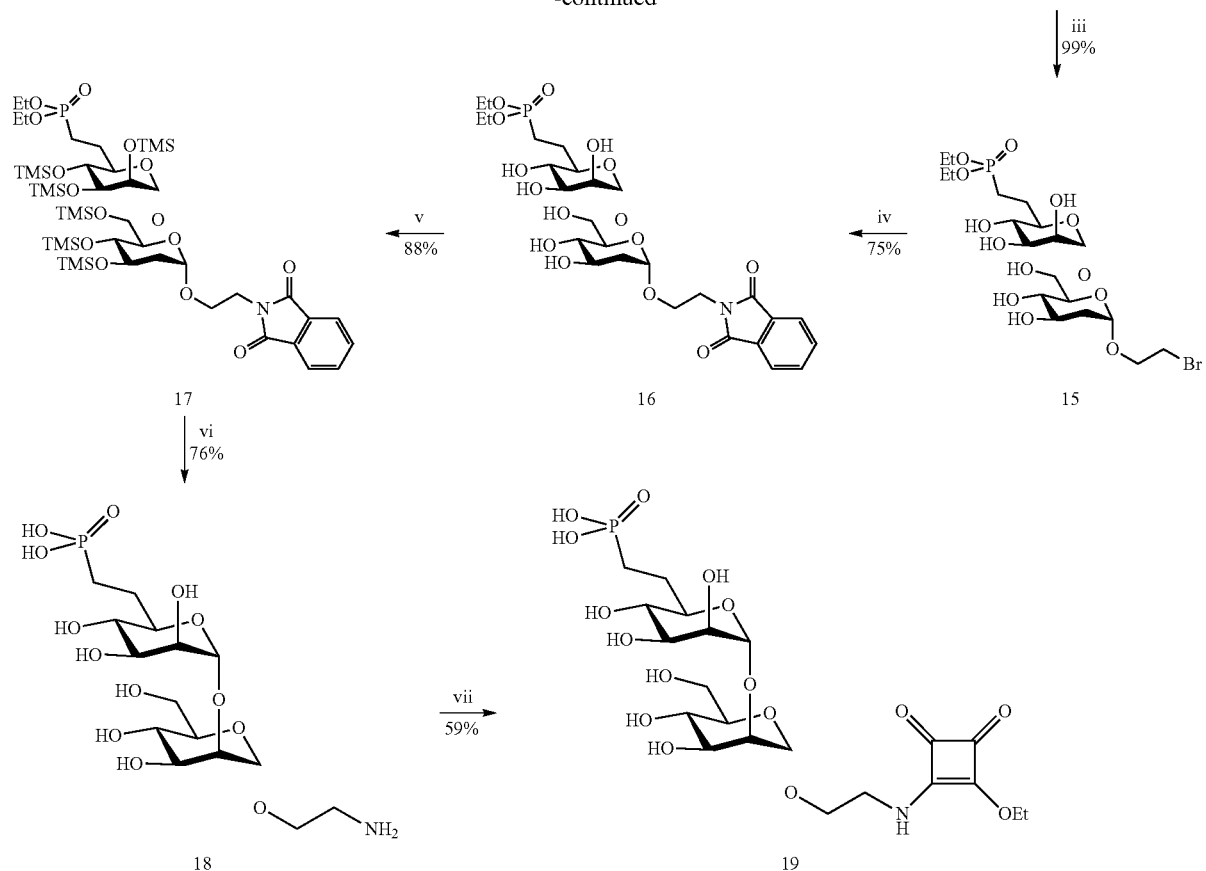

The alcohol 12 obtained as described previously is oxidized to aldehyde using Dess-Martin periodinane so as to form the compound 13. This key intermediate will allow access to the various disaccharides of formula (I).

In order to synthesize the "phosphonate" disaccharides of formula (I), the aldehyde 13 is reacted with tetraethyl methylenediphosphonate, deprotonated beforehand with sodium hydride, so as to form compound 14 with a yield of 75% over two steps. During a catalytic hydrogenation step, in the presence of palladium-on-carbon and for which the hydrogen is generated in situ by gradual addition of triethylsilane, the double bond and also the three benzyls are reduced and the trimethylsilyl groups are hydrolyzed. The compound 15 is thus obtained, without purification, with a quantitative yield. The bromine atom is then replaced with potassium phthalimide so as to form the intermediate 16 with a yield of 75%. The alcohol functions are then protected with trimethylsilyl chloride so as to give the compound 17 with a yield of 88%. The intermediate 17 thus obtained, without purification, is then reacted with trimethylsilyl chloride and sodium iodide so as to form bis(trimethylsilyl) phosphonate by a Rabinowitz type reaction. This intermediate is then converted to phosphonic acid through the action of hydrazine monohydrate in methanol, which will also displace the trimethylsilyl groups present on the secondary alcohols of the sugar and react with the phthalimide in order to mask the amine function. The compound 18 deprotected on the phosphonate part, on the alcohols of the two sugars, and bearing the amine function in the anomeric position is thus obtained, in a single step, with a yield of 76% over two steps. The compound 18 is then reacted with diethyl squarate so as to form the product 19 with a yield of 59%.

Conditions and reagents: (i) Dess-Martin periodinane, DCM, AT, 4 h (ii) tetraethyl methylenediphosphonate, NaH, THF, AT, 45 min; (iii) Pd/C, $Et_3SiH$, MeOH; (iv) potassium phthalimide, DMF, 60° C., 40 h; (v) TMSCl, $NEt_3$, DCM, DMF, AT, 24 h; (vi)-a TMSCl, NaI, ACN, 35° C., 1 h; (vi)-b $N_2H_4 \cdot H_2O$, MeOH, AT, 1 h30; (vii) diethyl squarate, EtOH/ $H_2O$, $NEt_3$.

Experimental Section

Preparation of bromoethyl 2,3,4-tri-O-trimethylsilyl-α-D-manno-hexodialdopyranosyl-(1→2)-3,4,6-tri-O-benzyl-α-D-mannopyranoside 13

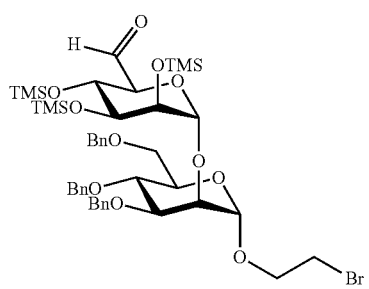

13

1 g (1 eq; 1.07 mmol) of the compound 12 is dissolved in 24 ml of DCM on molecular sieve. 5.4 ml (1.5 eq; 1.6 mmol)

of a solution of Dess-Martin periodinane at 0.3 M in dichloromethane are added dropwise. The reaction medium is stirred at ambient temperature for 4 h and then diluted with 120 ml of Et$_2$O. 25 ml of a saturated solution of NaHCO$_3$ and 3.9 g of Na$_2$S$_2$O$_3$ are added. The solution is stirred at ambient temperature for 5 min. The aqueous phase is extracted with 3×125 ml of Et$_2$O. The organic phases are combined, dried over MgSO$_4$ and concentrated so as to give the compound 13 that is used directly for the next step.

C$_{44}$H$_{65}$BrO$_{11}$Si$_3$      Chemical formula 13:

Molar mass: 934.14 g·mol$^{-1}$

R$_f$: 0.77 [DCM/Et$_2$O (95:5)]

Preparation of bromoethyl 2,3,4-tri-O-trimethylsilyl-6,7-dideoxy-7-diethoxyphosphinyl-αD-mannohept-6-enopyranosyl-(1→2)-3,4,6-tri-O-benzyl-α-D-mannopyranoside 14

14

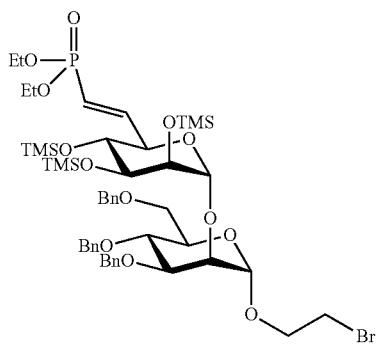

90 mg (2.5 eq; 2.67 mmol) of NaH as a 60% dispersion in oil are dissolved in 16 ml of THF. 530 µl (2 eq; 2.14 mmol) of tetraethyl methylenediphosphonate are added dropwise. The reaction mixture is stirred for 45 min at ambient temperature and then added to 998 mg (1 eq; 1.07 mmol) of the compound 13 dissolved in 8 ml of THF. The solution turns yellow in color and then becomes brown. The reaction medium is stirred at ambient temperature for 45 min and then diluted with 200 ml of CH$_2$Cl$_2$ and washed with 2×40 ml of brine. The aqueous phase is extracted with 3×130 ml of CH$_2$Cl$_2$. The organic phases are combined, dried over MgSO$_4$ and concentrated. The residue obtained (brown oil) is purified by automated flash chromatography on silica gel (DCM/Et$_2$O: 0% to 5% in 15 min; 5% for 10 min; from 5% to 10% in 15 min; 10% for 10 min; from 10 to 13% in 15 min) so as to give the compound 14 in the form of a light yellow oil with a yield of 76% (864 mg; 0.81 mmol) over two steps.

C$_{49}$H$_{76}$BrO$_{13}$Si$_3$      Chemical formula 14:

Molar mass: 1068.25 g·mol$^{-1}$

R$_f$: 0.26 [DCM/Et$_2$O (95:5)]

Preparation of bromoethyl 6-deoxy-6-diethoxyphosphinylmethylene-α-D-mannopyranosyl-(1→2)-α-D-mannopyranoside 15

15

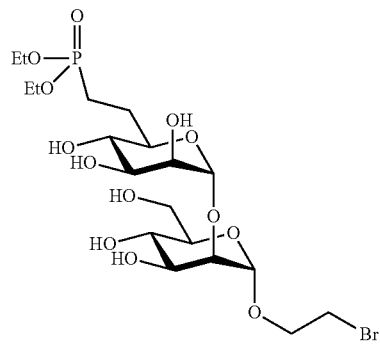

864 mg (0.81 mmol) of the compound 14 are dissolved in 8.2 ml of methanol. 130 mg (15% by weight) of palladium-on-carbon are added. 1.3 ml (8.1 mmol; 10 eq) of triethylsilane are added dropwise for 1 h20. The suspension is stirred at ambient temperature for 30 min and then filtered through celite. The filtrate is evaporated so as to give the compound 15 with a yield of 99% (468 mg; 8.0 mmol).

C$_{19}$H$_{36}$BrO$_{13}$P      Chemical formula 15:

Exact weight: 582.2 g·mol$^{-1}$

R$_f$: 0.23 [DCM/MeOH (85:15)]

MS, ESI$^+$ m/z: 583.1 [M+H]$^+$

Preparation of phthalimidoethyl 6-deoxy-6-diethoxyphosphinylmethylene-α-D-mannopyranosyl-(1→2)-α-D-mannopyranoside 16

16

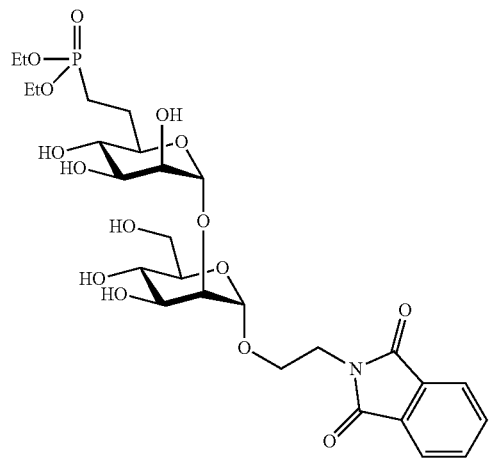

220 mg (0.38 mmol) of the compound 15 are dissolved in 1.8 ml of DMF on molecular sieve. 119 mg (0.64 mmol; 1.7 eq) of potassium phthalimide are added. The suspension is stirred for 40 h at 60° C. and then cooled to ambient temperature and concentrated. The residue obtained is purified by chromatography on silica gel (EtOAc/MeOH: 75/25) so as to give the compound 16 in the form of a colorless solid with a yield of 75% (184 mg; 0.28 mmol).

C$_{27}$H$_{40}$NO$_{15}$P      Chemical formula 16:

Molar mass: 649.58 g·mol$^{-1}$

R$_f$: 0.31 [EtOAc/MeOH (75:25)]

MS, ESI$^+$ m/z: 650.3 [M+H]$^+$

Preparation of phthalimidoethyl 2,3,4-tri-O-trimethylsilyl-6-deoxy-6-diethoxyphosphinylmethylene-α-D-mannopyranosyl-(1→2)-3,4,6-tri-O-trimethylsilyl-α-D-mannopyranoside 17

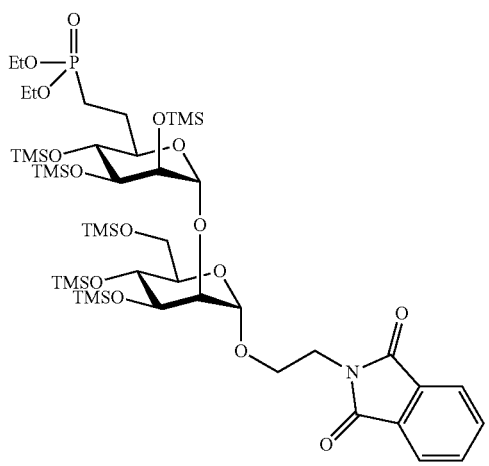

17

184 mg (0.28 mmol) of the compound 16 are dissolved in 817 µl of freshly distilled DCM and 1.15 ml (8.5 mmol; 30 eq) of triethylamine. The starting product is not completely soluble. 431 µl (3.4 mmol; 12 eq) of trimethylsilyl chloride are added dropwise. The solution is stirred at ambient temperature for 15 h. The starting product is still not completely dissolved and the solution is white in color. 0.5 ml of DMF on molecular sieve are added, the starting product is then soluble. The solution is stirred at ambient temperature for 24 h and then evaporated. During the reaction, the solution becomes brown. The brown residue is dissolved in cyclohexane and then filtered through celite. The filtrate is concentrated so as to give the compound 17 with a yield of 88% (268 mg; 0.25 mmol) which is directly used for the next step.

C$_{45}$H$_{88}$NO$_{15}$PSi$_6$      Chemical formula 17:

Molar mass: 1082.66 g·mol$^{-1}$

R$_f$: 0.49 [DCM/Et$_2$O (9:1)]

Preparation of aminoethyl 6-deoxy-6-dihydroxyphosphinylmethylene-α-D-mannopyranosyl-(1→2)-D-mannopyranoside (M6Pn-α(1,2)-Man-Ethyl-NH$_2$) 18

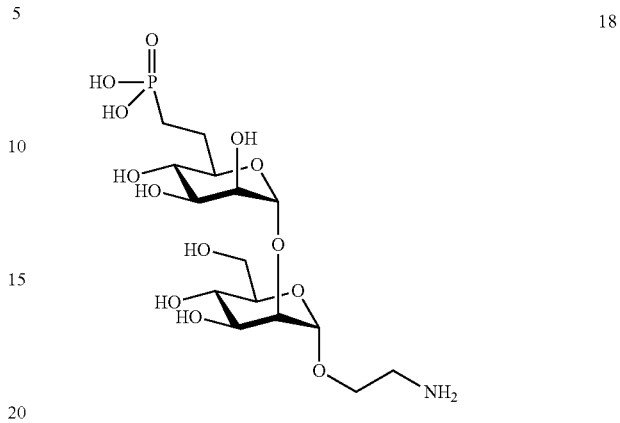

18

269 mg (0.25 mmol) of the compound 17 and 260 mg (1.73 mmol; 7 eq) of sodium iodide are dissolved in 7.3 ml of freshly distilled acetonitrile. 219 µl (1.73 mmol; 7 eq) of trimethylsilyl chloride are added dropwise. The solution is stirred at 35° C. for 1 h15. A precipitate forms during the reaction. The supernatant is drawn off with a tube into a round-bottomed flask and evaporated to dryness. 132 µl (2.72 mmol; 11 eq) of hydrazine monohydrate are diluted in 3.4 ml of methanol on molecular sieve and added to the previously obtained residue. A white precipitate is formed. The suspension is stirred at ambient temperature for 1 h30. The precipitate is dissolved in water and evaporated. The residue obtained is purified by chromatography on silica gel (isopropanol/aqueous ammonia/water: 5/3/2) so as to give the compound 18 in the form of a white solid with a yield of 76% (67 mg; 0.14 mmol).

C$_{15}$H$_{30}$NO$_{13}$P      Chemical formula 18:

Molar mass: 463.37 g·mol$^{-1}$

R$_f$: 0.49 [DCM/Et$_2$O (9:1)]

HRMS: mass calculated: 464.1533; mass found: 464.1530.

Preparation of (4-ethoxy-2,3-dioxocyclobut-1-enyl) aminoethyl 6,7-dideoxy-7-dihydroxyphosphinyl-α-D-manno-heptopyranosyl-(1→2)-α-D-mannopyranoside (M6Pn-α(1,2)-Man-EthylSq) 19

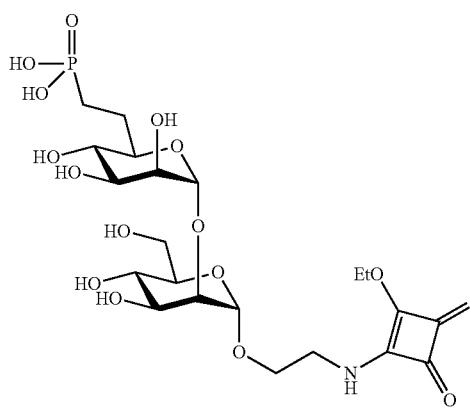

19

The compound 18 (32 mg; 1 eq; 0.07 mmol) is dissolved in an ethanol/water mixture (1:1) (620 μl). Diethyl squarate (10.3 μl; 1 eq; 0.07 mmol) and triethylamine (9.7 μl; 1 eq; 0.07 mmol) are added. The reaction is stirred at ambient temperature for 20 h and the solvent is then evaporated off. The residue is precipitated from an EtOAc/MeOH mixture (7:3). After centrifugation, the precipitate is rinsed five times with ethyl acetate so as to give the compound 19 with a yield of 59% (24 mg; 0.041 mmol).

$C_{21}H_{34}NO_{16}P$   Chemical formula 19:

Molar mass: 587.47 g·mol$^{-1}$ $R_f$: 0.67 [MeOH/H$_2$O (9:1)]

MS, ESI m/z: 586 [M−H]$^-$

3) Preparation of Disaccharides 20, 21, 22, 23, 24, and 25 Corresponding to the Formula (I) in which X Represents the Carboxylate Group The process for preparing disaccharides 20, 21, 22, 23, 24 and 25 corresponding to the formula (I) in which X represents the carboxylate group is illustrated below:

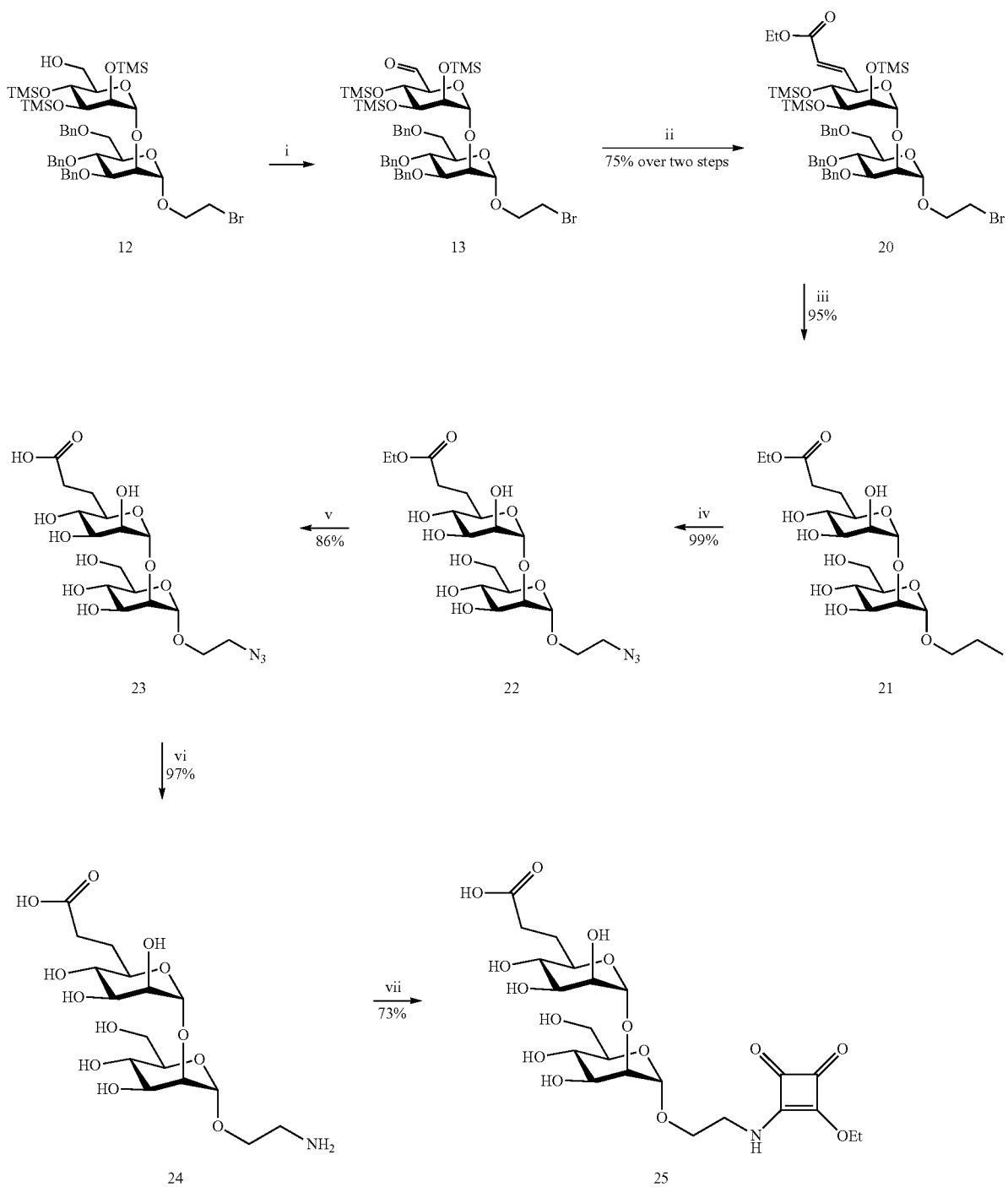

The beginning of the synthesis of the "carboxylate" disaccharides of formula (I) is identical to that of the "phosphonate" disaccharides, namely the aldehyde 13 is obtained from the alcohol 12 in the same way as described above.

The aldehyde 13 is then reacted with triethyl phosphonoacetate deprotonated beforehand using sodium hydride so as to form the compound 20 with a yield of 75% over two steps. The double bond and also the three benzyl groups are reduced in a single hydrogenation step. During this reaction, the trimethylsilyl groups are also hydrolyzed. This reaction is carried out using palladium-on-carbon at 10% and the hydrogen is generated in situ by gradual addition of triethylsilane so as to form the compound 21 with a yield of 95%. This hydrogenation step is total and does not require purification in order to obtain the pure compound 21. The bromine atom is then substituted with sodium azide so as to give the compound 22 with a yield of 99%. The ester function is then saponified so as to form the compound 23 with a yield of 86%. Finally, the azide function is reduced during a catalytic hydrogenation reaction using palladium-on-carbon and triethylsilane so as to form the compound 24 with a yield of 97%. Finally, the compound 24 is reacted with diethyl squarate so as to give the compound 25 with a yield of 73%.

Conditions and reagents: (i) Dess-Martin periodinane, DCM, AT, 4 h; (ii) triethyl phosphonoacetate, NaH, THF, AT, 14 h; (iii) Pd/C, Et$_3$SiH, MeOH, AT; (iv) NaN$_3$, DMF, AT, 5d; (v) 1N NaOH, AT, 20 h; (vi) Pd/C, Et$_3$SiH, MeOH/H$_2$O; (vii) diethyl squarate, EtOH/H$_2$O, NEt$_3$, AT, 2 h30.

Experimental Section

Preparation of bromoethyl 2,3,4-tri-O-trimethylsilyl-6,7-dideoxy-7-ethoxycarbonyl-α-D-manno-hept-6-enopyranosyl-(1→2)-3,4,6-tri-O-benzyl-α-D-mannopyrannoside 20

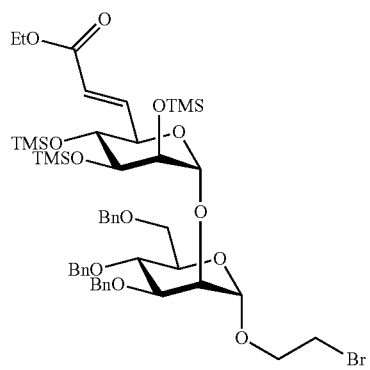

20

144 mg (4 eq; 4.28 mmol) of NaH 60% dispersion in oil are dissolved in 10 ml of THF. 637 μl (3 eq; 3.21 mmol) of triethyl phosphonoacetate are added dropwise. The reaction mixture is stirred for 45 min at ambient temperature and then added to 1.065 g (1 eq; 1.07 mmol) of the compound 13 dissolved in 20 ml of THF. The solution turns orange. The reaction medium is stirred at ambient temperature for 14 h30 and then diluted with 175 ml of CH$_2$Cl$_2$ and washed with 4×50 ml of brine. The aqueous phase is extracted with 125 ml of CH$_2$Cl$_2$. The organic phases are combined, dried over MgSO$_4$ and concentrated. The residue obtained (orange oil) is purified by automated flash chromatography on silica gel (Cyclohexane/Et$_2$O: 20% (900 ml)) so as to give the compound 20 in the form of a colorless oil with a yield of 75% (802 mg; 0.80 mmol) over two steps.

C$_{48}$H$_{71}$BrO$_{12}$Si$_3$     Chemical formula 20:

Molar mass: 1004.23 g·mol$^{-1}$

R$_f$: 0.39 [Cyclo/Et$_2$O (8:2)]

Preparation of bromoethyl 6,7-dideoxy-7-ethoxycarbonyl-α-D-manno-heptopyranosyl-(1→2)-α-D-mannopyranoside 21

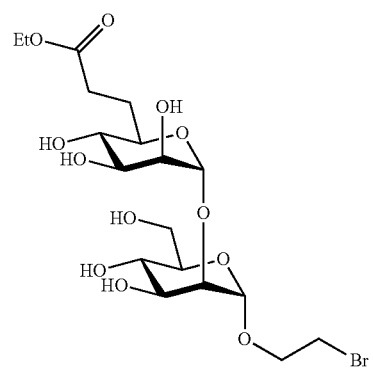

21

795 mg (1 eq; 0.79 mmol) of the compound 20 are dissolved in 8 ml of methanol. 160 mg (20% by weight) of palladium-on-carbon at 10% are added. 1.3 ml (10 eq; 7.9 mmol) of triethylsilane are added dropwise for 1 h. The reaction medium is stirred at ambient temperature for 20 min and then filtered through celite (rinsed with hot methanol). The filtrate is concentrated so as to give the compound 21 in the form of a colorless oil with a yield of 95% (390 mg; 0.75 mmol).

C$_{18}$H$_{31}$BrO$_{12}$     Chemical formula 21:

Molar mass: 519.34 g·mol$^{-1}$

R$_f$: 0.40 [DCM/MeOH (85:15)]

Preparation of azidoethyl 6,7-dideoxy-7-ethoxycarbonyl-α-D-manno-heptopyranosyl-(1→2)-α-D-mannopyranoside 22

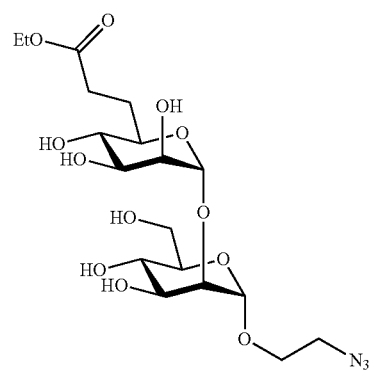

22

440 mg (1 eq; 0.85 mmol) of the compound 21 are dissolved in 3.5 ml of freshly distilled DMF. 66 mg (1.2 eq;

1.02 mmol) of sodium azide are added. The solution is stirred at ambient temperature for five days and then evaporated. The residue obtained is purified by flash chromatography on silica gel (EtOAc/MeOH: 10% (210 ml); 20%) so as to give the compound 22 in the form of a white solid with a yield of 99% (407 mg; 0.85 mmol).

$C_{18}H_{31}N_3O_{12}$      Chemical formula 22:

Molar mass: 481.45 g·mol$^{-1}$
$R_f$: 0.43 [EtOAc/MeOH (8:2)]
MS, ESI$^+$ m/z: 482 [M+H]$^+$ Preparation of azidoethyl 6,7-dideoxy-7-hydroxycarbonyl-α-D-manno-heptopyranosyl-(1→2)-α-D-mannopyranoside 23

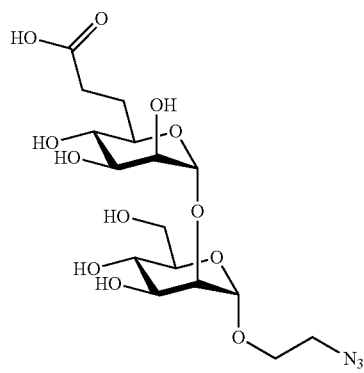

23

377 mg (1 eq; 0.78 mmol) of the compound 22 are dissolved in 932 µl (1.2 eq; 0.932 mmol) of a 1 N sodium hydroxide solution. The solution is stirred at ambient temperature for 20 h and then concentrated. The residue obtained is purified by flash chromatography on silica gel (isopropanol/35% aqueous ammonia/water: 6/3/1) so as to give the compound 23 in the form of a white solid with a yield of 86% (316 mg; 0.67 mmol).

$C_{16}H_{27}N_3O_{12}$      Chemical formula 23:

Molar mass: 453.40 g·mol$^{-1}$
$R_f$: 0.38 [isopropanol/NH$_4$OH/water (6:3:1)]
MS, ESI$^+$ m/z: 454 [M–H]$^+$ Preparation of aminoethyl 6,7-dideoxy-7-hydroxycarbonyl-α-D-manno-heptopyranosyl-(1→2)-α-D-mannopyranoside (M6C-α(1,2)-Man-Ethyl-NH$_2$) 24

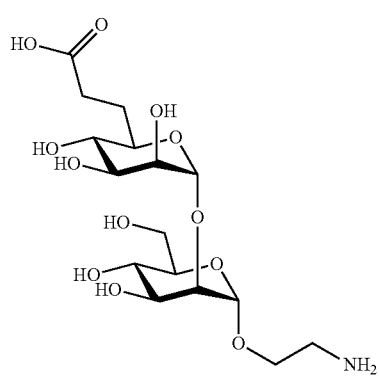

24

316 mg (1 eq; 0.67 mmol) of the compound 23 are dissolved in 15 ml of a 2:1 methanol/water mixture. 32 mg (10% by weight) of palladium-on-carbon at 10% are added. 536 µl (5 eq; 3.36 mmol) of triethylsilane are added dropwise for 40 min. After stirring for 45 min at ambient temperature, the starting product is still present. 536 µl (5 eq; 3.36 mmol) of triethylsilane are added dropwise for 30 min. The reaction medium is stirred at ambient temperature for 10 min (no change) and then filtered through celite (rinsed with hot methanol). The filtrate is concentrated and then dissolved in 3 ml of a 2:1 methanol/water mixture. 60 mg (20% by weight) of palladium-on-carbon at 10% are added. 1.07 ml (10 eq; 6.72 mmol) of triethylsilane are added dropwise for 20 min. The suspension is stirred at ambient temperature for 30 min and then filtered through celite (rinsed with hot methanol). The filtrate is concentrated so as to give the compound 24 in the form of a colorless oil with a yield of 97% (280 mg; 0.66 mmol).

$C_{16}H_{29}NO_{12}$      Chemical formula 24:

Molar mass: 427.40 g·mol$^{-1}$
$R_f$: 0.51 [isopropanol/NH$_4$OH/water (5:4:1)]
MS, ESI$^+$ m/z: 428 [M+H]$^+$ Preparation of (4-ethoxy-2,3-dioxocyclobut-1-enyl) aminoethyl 6,7-dideoxy-7-hydroxycarbonyl-α-D-manno-heptopyranosyl-(1→2)-α-D-mannopyranoside (M6C-α(1,2)-Man-EthylSq) 25

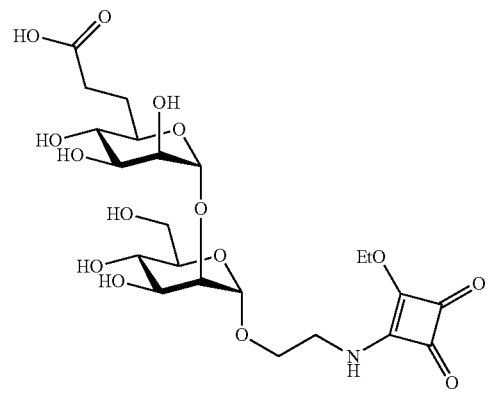

25

45 µl (1 eq; 0.307 mmol) of diethyl squarate are diluted in 300 µl of a 2:1 ethanol/water mixture. The pH of the solution is 5. 20 µl (0.5 eq; 0.154 mmol) of triethylamine are added so as to achieve a pH of 8-9. 131 mg (1 eq; 0.307 mmol) of the compound 24 dissolved in 1.7 ml of a 2:1 ethanol/water mixture are added dropwise. The solution is stirred at ambient temperature for 2 h30, while maintaining the pH at 8-9 by adding triethylamine, and is then concentrated. The residue obtained is purified by flash chromatography on silica gel (EtOAc/MeOH: deposition 3:7; elution: 30% (20 ml); 40% (10 ml); 50% (20 ml); 70% (30 ml) so as to give the compound 25 in the form of a colorless solid with a yield of 73% (123 mg; 0.223 mmol).

$C_{22}H_{33}NO_{15}$      Chemical formula 25:

Molar mass: 551.50 g·mol$^{-1}$
$R_f$: 0.36 [EtOAc/MeOH (1:1)]
MS, ESI$^+$ m/z: 552 [M+H]$^+$

EXAMPLE 2

Study of the Disaccharide Analogs 18, 19, 24 and 25 of the Invention, Corresponding to the General Formula (I)

1) Binding of the M6P Analogs of the Invention with CI-M6PR

96-Well plates (Maxisorp Nunc) are incubated overnight at 4° C. with 200 µl of PMP (pentamannose 6-phosphate) at the concentration of 200 µg·ml$^{-1}$, in carbonate buffer (NaHCO$_3$/Na$_2$CO$_3$ at 0.1M, pH 9.6). The following day, the solution containing the residual PMP is discarded and the wells are saturated, for 1 h at ambient temperature, with 360 µl of 1% gelatin (Type A from Porcine Skin) diluted in PBS (1.9 mM NaH$_2$PO$_4$, 8.1 mM Na$_2$PO$_4$ and 154 mM NaCl, pH 7.4). The wells are then rinsed five times with PBS to which 0.2% gelatin has been added. All the washes and also the dilutions are carried out in the solution of PBS to which 0.2% gelatin has been added. The M6P analogs to be tested at the various concentrations (from $10^{-2}$ to $10^{-7}$ M) are pre-incubated in the presence of pre-biotinylated CI-M6PR (M6PRb) (2.5 µg·mol$^{-1}$) for 20 min, then 200 µl of the mixture are incubated in the wells for 2 h, at ambient temperature. After three washes, the wells are incubated for 1 h with a streptavidin-peroxidase solution (250 µl per well; 3.10$^{-8}$ M). After three more washes, 200 µl of a solution of OPD (o-phenylenediamine, 1 mg·ml$^{-1}$ in citrate buffer, pH 5.0, and 1 µl 30% H$_2$O$_2$.ml$^{-1}$; Sigma Aldrich) are added. After incubation for 20 min in the dark at ambient temperature, the optical densities are measured at the wavelength of 450 nm.

The affinities of the phosphonate disaccharide 18 and carboxylate disaccharide 24 of formula (I) of the invention were measured and compared with those of their respective monosaccharide homologs.

The affinity denotes the binding capacity (in the case in point by means of a covalent bond) of the M6P analogs for CI-M6PR.

The relative affinity makes it possible to compare the affinity of the molecules with M6C-Ethyl-NH$_2$ taken as reference and to which a value equal to 1 is assigned.

The results obtained are summarized in table 1 below.

The affinity of the phosphonate disaccharide 18 (row 1 of table 1), aminoethyl 6-deoxy-6-dihydroxyphosphinylmethylene-α-D-mannopyranose-α-(1,2)-D-mannopyrannose, represented by M6Pn-α(1,2)-Man-Ethyl-NH$_2$, is thus compared with that of the phosphonate monosaccharide (row 2), represented M6Pn-Ethyl-NH$_2$.

The affinity of the carboxylate disaccharide 24 (row 3), aminoethyl 6,7-dideoxy-7-hydroxycarbonyl-α-D-manno-hept-6-anopyranose-α-(1,2)-α-D-mannopyrannose, represented by M6C-α(1,2)-Man-Ethyl-NH$_2$, is thus compared with that of the carboxylate monosaccharide (row 4), represented M6C-Ethyl-NH$_2$.

TABLE 1

| M6P analogs | Chemical structure | IC$_{50}$ in M | Relative affinity |
|---|---|---|---|
| Compound 18 of the invention M6Pn-α(1,2)-Man-Ethyl-NH$_2$ | 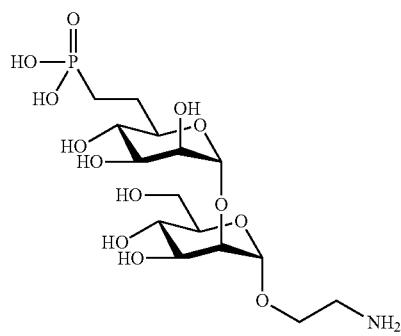 | 0.5 × 10$^{-5}$M | 19.8 |
| M6Pn-Ethyl-NH$_2$ | 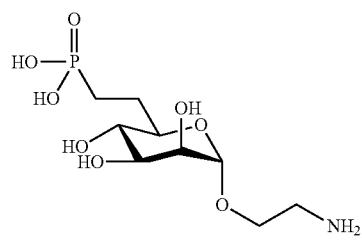 | 2.9 × 10$^{-5}$M | 3.4 |

TABLE 1-continued

| M6P analogs | Chemical structure | IC$_{50}$ in M | Relative affinity |
|---|---|---|---|
| Compound 24 of the invention M6C-α(1,2)-Man-Ethyl-NH$_2$ | 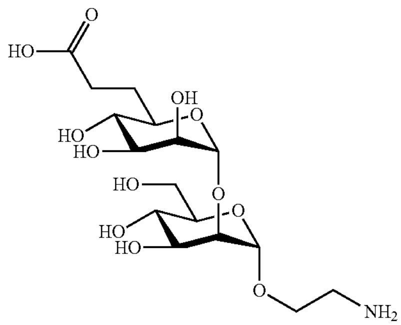 | $1.7 \times 10^{-5}$M | 5.8 |
| M6C-Ethyl-NH$_2$ | 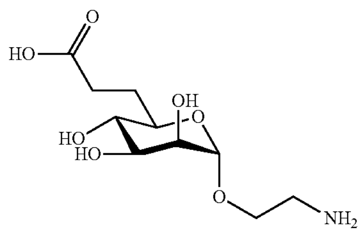 | $9.9 \times 10^{-5}$M | 1 |

Conclusion:

A better affinity of the disaccharide analogs 18 and 24 of the invention is observed for CI-M6PR than that of the same analogs that are monosaccharide analogs. Furthermore, a gain in affinity of the phosphonate analog 18 is observed compared with the carboxylate analog 24, both in the disaccharide series and in the monosaccharide series.

2) Evaluation of the Cytotoxicity of the M6P Analogs of the Invention with CI-M6PR The cytotoxicity of the phosphonate disaccharide analogs 18, 19 and carboxylate disaccharide analogs 24, 25 of the invention was evaluated on LNCaP prostate cancer cells, and was compared with that of their respective monosaccharide homologs.

The disaccharide analogs 18, 19, 24 and 25 of formula (I) of the invention and also the monosaccharide analogs of the disaccharide analogs 19, 24 and 25 are tested:

M6Pn-α(1,2)-Man-Ethyl-NH$_2$ (compo 18);
M6Pn-α(1,2)-Man-EthylSq (compo 19);
M6Pn-EthylSq (described below);
M6C-α(1,2)-Man-Ethyl-NH$_2$ (compo 24);
M6C-Ethyl-NH$_2$ (described in table 1);
M6C-α(1,2)-Man-EthylSq (compo 25);
M6C-EthylSq (described below).

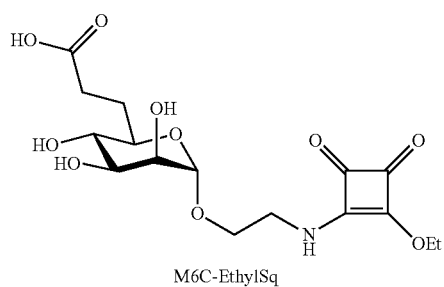

M6C-EthylSq

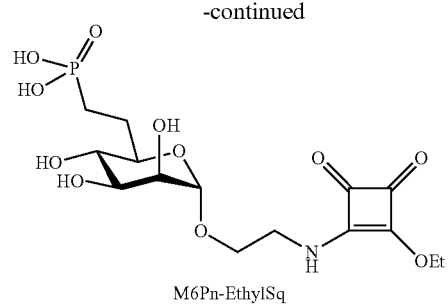

M6Pn-EthylSq

Experimental Protocol

The LNCaP human prostate cancer cells are incubated with solutions of the analogs as described above having concentrations ranging from $10^{-3}$ M to $10^{-7}$ M.

The cell survival is measured after four days of incubation by means of an MTS (3-(4,5-dimethylthiazol-2-yl)-5-(3-carboxymethoxyphenyl)-2-(4-sulfophenyl)-2H-tetrazolium) test. This compound is reduced by a mitochondrial enzyme and will form an orangy-yellow colored compound which is soluble in an aqueous medium. The measurement of the optical densities thus indicates the amount of live cells. The cell growth results were determined with respect to a control treated only with the carrier (solution in which the analogs are diluted).

The results obtained are represented in FIG. 1.

Conclusion:

None of the compounds tested shows any significant cytotoxicity on LNCaP human cells even at very high concentrations (up to $10^{-3}$ M).

Thus, the M6P analogs tested do not show any intrinsic toxicity for cells expressing CI-M6PR, such as LNCaP cells.

3) Functionalization of Nanoparticles for Single-Photon Photodynamic Therapy

A compound of interest Ⓨ, namely mesoporous silica nanoparticles incorporating a photosensitizer of neutral porphyrin type, is then surface-functionalized with:

the phosphonate disaccharide analog M6Pn-α(1,2)-Man-EthylSq (19) and the carboxylate disaccharide analog M6C-α(1,2)-Man-EthylSq (25);

the phosphonate monosaccharide analog M6Pn-EthylSq and the carboxylate monosaccharide analog M6C-EthylSq.

The structure of the neutral porphyrin used for the photodynamic therapy is represented below:

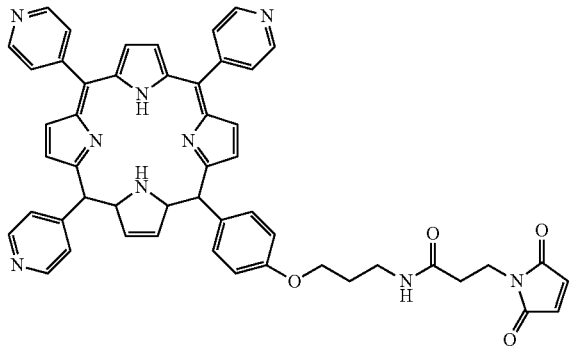 [SMILES: O=C(CCN1C(=O)C=CC1=O)NCCCOc1ccc(C2C3=N/C(=C(/c4ccncc4)c4ccc([nH]4)/C(c4ccncc4)=C4/C=CC(=N4)C(c4ccncc4)C4C=CC2N4)C=C3)cc1]

Preparation of the Silica Nanoparticles Incorporating the Porphyrin

The porphyrin must bear a trialkoxysilane group which will enable it to be incorporated into the siliceous network during the sol-gel process described below. For this, the porphyrin is reacted with 3-mercaptopropyltrimethoxysilane in methanol at ambient temperature for 12 h.

the carboxylate disaccharide analog M6C-α(1,2)-Man-EthylSq (25) and the phosphonate disaccharide analog M6Pn-α(1,2)-Man-EthylSq (19).

The functionalization is carried out in two steps; the first step consists in introducing amine functions onto the surface of the nanoparticles which, in the second step, will replace the ethoxy group present on the squarate of the arm of the analog. The nanoparticles are reacted with aminopropyltriethoxysilane (APTS) in a water/ethanol mixture (2:1). The pH of the reaction medium is adjusted to 6 by adding a 0.2 M HCl solution and then stirred at ambient temperature for 20 h. The nanoparticles are obtained after several steps of washing with ethanol, followed by centrifugations.

For the coupling of the carboxylate analogs (M6CEthylSq and M6C-α(1,2)-Man-EthylSq (25)), the analog was dissolved in an ethanol/water mixture (1:1) in the presence of the nanoparticles and then the suspension was heated at 50° C. for 12 h.

It should be noted that triethylamine can be added in order to maintain the pH at 8-9 and to promote coupling of the analogs to the nanoparticles.

After steps of washing with water and with ethanol, the nanoparticles functionalized with the carboxylate analogs are obtained.

The coupling (grafting) of the carboxylate disaccharide analog M6C-α(1,2)-Man-EthylSq (25) with the silica nanoparticles incorporating porphyrin (represented by a star) is represented below:

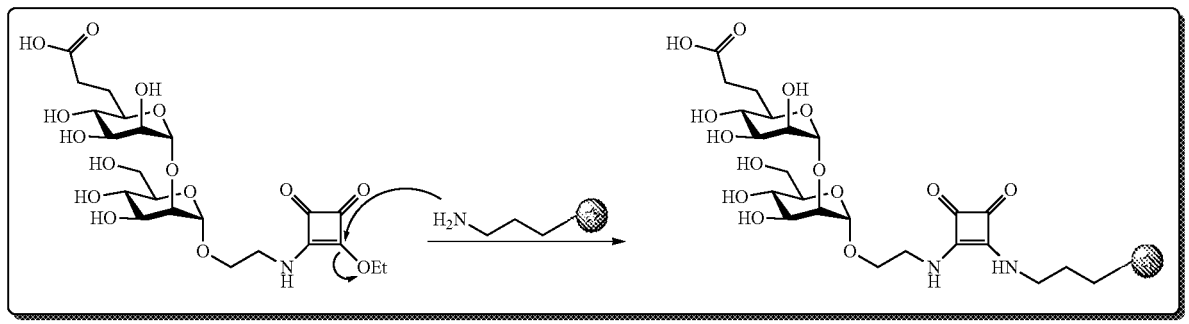

CTAB (cetyltrimethylammonium bromide) is dissolved in a 0.2 M sodium hydroxide solution. Micelles will thus form in the solution. The silylated porphyrin and then TEOS (tetraethyl orthosilicate) are added. The reaction medium is quickly diluted with a large volume of water in order to lower the pH to 8-8.5 and to initiate condensation. After 6 min, the reaction medium is neutralized with a 0.2 M HCl solution. The nanoparticles are obtained after steps of washing with ammonium nitrate in order to remove the CTAB contained in the pores.

During the synthesis of the nanoparticles, the reaction times and also the pH must be meticulously controlled in order to control the size of the nanoparticles formed. The nanoparticles thus obtained have a hydrodynamic diameter of approximately 200 nm and contain 11 μg of porphyrin per gram of nanoparticle.

Functionalization of the Nanoparticle Surface

These nanoparticles are then surface-functionalized with the carboxylate monosaccharide analog M6CEthylSq and the phosphonate monosaccharide analog M6PnEthylSq and A conjugate of formula (III) is thus obtained.

Since the squarate group can be observed by UV, the amount of monosaccharides and disaccharides was assayed by UV/visible spectroscopy.

Table 2 below represents the amount of porphyrin incorporated (in μg/g) and the amount of monosaccharide or disaccharide (in μmol/g) grafted onto the nanoparticles.

The abbreviation "MSN" represents the mesoporous silica nanoparticles alone, without grafting with the monosaccharide or the disaccharide.

The M6CEthylSq, M6C-α(1,2)-Man-EthylSq (25) and M6Pn-α(1,2)-Man-EthylSq (19) analogs grafted with the mesoporous silica nanoparticles are represented by MSN-M6C-EthylSq; MSN-M6C-α(1,2)-Man-EthylSq and MSN-M6Pn-α(1,2)-Man-EthylSq. These compounds are conjugates corresponding to the general formula (III).

TABLE 2

| Nanoparticles | Amount of porphyrin (μmol/g) | Amount of mono- or disaccharide (μmol/g) |
|---|---|---|
| MSN | 11 μmol/g | — |
| MSN-M6C-EthylSq | 11 μmol/g | 351 μmol/g |
| MSN-M6C-α(1,2)-Man-EthylSq | 11 μmol/g | 329 μmol/g |
| MSN-M6Pn-α(1,2)-Man-EthylSq. | 11 μmol/g | 167 μmol/g |

In Vitro Evaluation in Photodynamic Therapy

The MSN-M6C-EthylSq and MSN-M6C-α(1,2)-Man-EthylSq carboxylate conjugates of formula (III) were used in in vitro PDT experiments on LNCaP prostate cancer cells which overexpress CI-M6PR.

The LNCaP cells were incubated with 80 μg·mol$^{-1}$ of nanoparticles alone (MSN) or with 80 μg·mol$^{-1}$ of nanoparticles functionalized with the mono- or disaccharide (i.e. with 80 μg·mol$^{-1}$ of MSN-M6C-EthylSq and MSN-M6C-α(1,2)-Man-EthylSq conjugates) for 3, 6, 9 or 18 h, then irradiated for 20 min with a laser at 650 nm (3 mW, 11.25 J·cm$^{-2}$).

The MTS cell survival test was carried out 48 h after the irradiation.

After incubation for three hours, a very slight increase in the phototoxic effect of the nanoparticles functionalized with the mono- or disaccharides is observed.

When the incubation time is increased to 6 h, it is noted that the functionalization with a carboxylate disaccharide brings a strong improvement in the phototoxic effect, with 73% cell death compared with 35% for the carboxylate monosaccharide. This is linked to the improvement in the recognition of CI-M6PRs resulting in a faster internalization of the nanoparticles (functionalized with a disaccharide) into the cells.

These results demonstrate the advantage of the functionalization of the nanoparticles with disaccharide analogs, making it possible both to reduce the incubation time and to considerably increase the phototoxic effect of the nanotools.

If the incubation time is increased to 9 h, the cell death obtained for the cells treated with the nanoparticles functionalized with the disaccharide reaches 81% compared with 55% for the nanoparticles functionalized with the monosaccharide.

In the case of an incubation for 18 h, an improvement in the phototoxic effect is observed for the nanoparticles functionalized with the monosaccharide carboxylate analogs compared with the effect of these same nanoparticles after an incubation of 9 h.

On the other hand, the effect of the disaccharide nanoparticles is not increased at 18 h since this effect is already at its maximum after 9 h of incubation.

The phototoxic effects of the nanoparticles alone (MSN) and the nanoparticles functionalized with the carboxylate monosaccharide (MSN-M6C-EthylSq) and carboxylate disaccharide (MSN-M6C-α(1,2)-Man-EthylSq) at the various incubation times are reproduced in FIG. 2.

Conclusion

The functionalization of nanoparticles with dimannosides that are analogs of M6P thus makes it possible to very significantly increase the phototoxic efficacy compared with the nanoparticles grafted with the monosaccharide analogs, while at the same time reducing the incubation time. This increase in efficacy associated with the affinity for CI-M6PR can be determined for the diagnostic or therapeutic application of the compounds of interest Ⓨ (nanoparticles, glycoproteins, small molecules, etc.), the metabolic clearance of which in human beings can be rapid.

EXAMPLE 3

Synthesis of Compounds of Formula (I)

Preparation of Disaccharides 26, 27 and 28 Corresponding to the Formula (I) in which X Represents the Phosphonate Group The process for preparing disaccharides 26, 27 and 28 corresponding to the formula (I) in which X represents the phosphonate group is illustrated below:

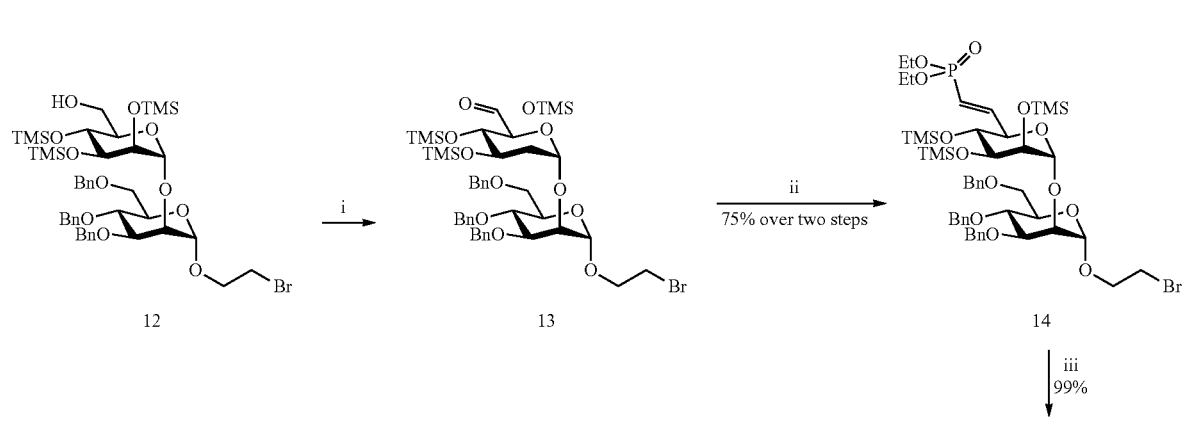

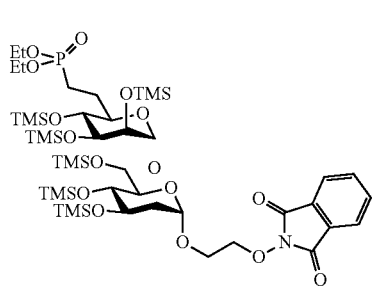 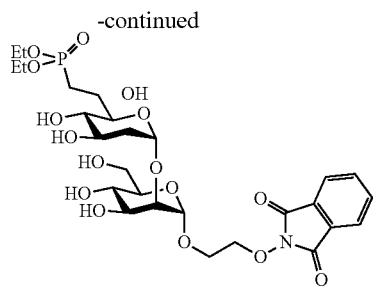 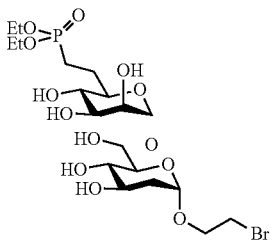

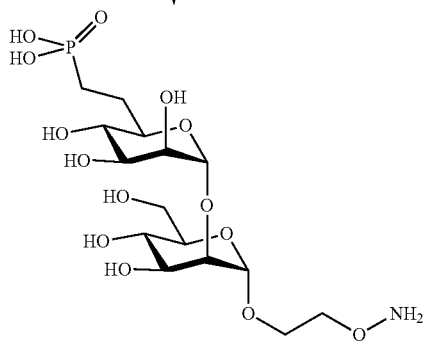

The beginning of the synthesis of the phosphonate disaccharide 28 of formula (I) is identical to that of the phosphonate disaccharide 19, namely the phosphonate 15 is obtained from the alcohol 12 in the same way as described above.

In order to synthesize the phosphonate disaccharide 28 of formula (I), the aldehyde 13 is reacted with tetraethyl methylenediphosphonate, deprotonated beforehand with sodium hydride, so as to form the compound 14 with a yield of 75% over two steps. During a catalytic hydrogenation step, in the presence of palladium-on-carbon and for which the hydrogen is generated in situ by gradual addition of triethylsilane, the double bond and also the three benzyls are reduced and the trimethylsilyl groups are hydrolyzed. The compound 15, is thus obtained, without purification, with a quantitative yield. The bromine atom is then replaced with N-hydroxyphthalimide so as to form the intermediate 26 with a yield of 68%. The alcohol functions are then protected with trimethylsilyl chloride so as to give the compound 27 with a yield of 88%. The intermediate 27 thus obtained, without purification, is then reacted with trimethylsilyl chloride and sodium iodide so as to form the bis(trimethylsilyl) phosphonate by a Rabinowitz type reaction. This intermediate is then converted into phosphonic acid through the action of hydrazine monohydrate in methanol which will also displace the trimethylsilyl groups present on the secondary alcohols of the sugar and react with the hydroxyphthalimide in order to unmask the oxyamine function. The compound 28 deprotected on the phosphonate part, and on the alcohols of the two sugars, and bearing in the anomeric position the oxyamine function, required for the coupling with the enzyme, is thus obtained in a single step, with a yield of 64% over two steps.

Conditions and reagents: (i) Dess-Martin periodinane, DCM, AT, 4 h (ii) tetraethyl methylenediphosphonate, NaH, THF, AT, 45 min; (iii) Pd/C, Et$_3$SiH, MeOH; (iv) N-hydroxyphthalimide, NaH, DMF, 65° C., 20 h; (v) TMSCl, NEt$_3$, DCM, DMF, AT, 24 h; (vi)-a TMSCl, NaI, Et$_3$N, ACN, 35° C., 4 h; (vi)-b N$_2$H$_4$.H$_2$O, MeOH, AT, overnight.

Experimental Section

Preparation of 2-N-oxyphthalimidoethyl 6-deoxy-6-diethoxyphosphinylmethylene-α-D-mannopyranosyl-(1→2)-α-D-mannopyranoside 26

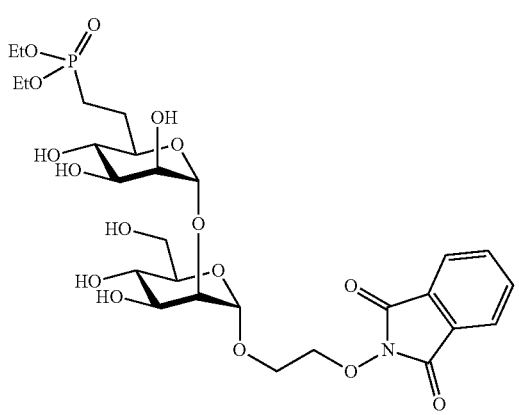

177 mg (2.2 eq, 5.3 mmol) of NaH are suspended in 80 ml of DMF. 783 mg (2 eq, 4.8 mmol) of N-hydroxyphthalimide are added (red solution). After stirring for one hour at 65° C. (dark red solution), 1.4 g (1 eq, 2.4 mmol) of the compound 15 dissolved in 20 ml of DMF are added. After 20 h at 65° C., the solution is cooled and the DMF is evaporated off under reduced pressure. The crude product obtained is purified on a silica gel column with an EtOAc/MeOH gradient (95:5→80:20) so as to give the compound 26 with a yield of 68% (1.08, 1.62 mmol).

$C_{27}H_{40}NO_{16}P$  Chemical formula 26:

Molar mass: 665.58 g·mol$^{-1}$ $R_f$: 0.6 [EtOAc/MeOH (70:30)]

Preparation of 2-N-oxyphthalimidoethyl 2,3,4-tri-O-trimethylsilyl-6-deoxy-6-diethoxyphosphinylmethylene-α-D-mannopyranosyl-(1→2)-3,4,6-tri-O-trimethylsilyl-α-D-mannopyranoside 27

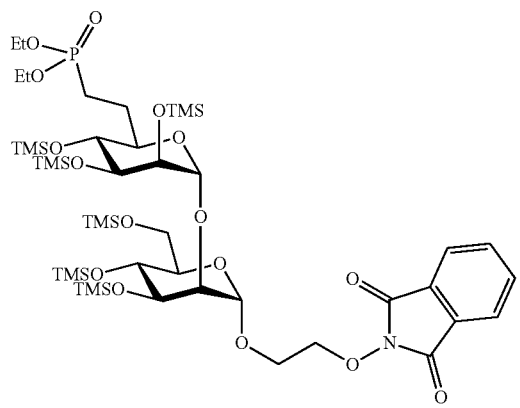

1.05 g (1 eq, 1.6 mmol) of the compound 26 are dissolved in 10 ml of freshly distilled DCM and 6.6 ml (47.3 mmol, 30 eq) of triethylamine. The starting product is not completely soluble. 2.4 ml (18.9 mmol, 12 eq) of trimethylsilyl chloride are added dropwise. The solution is stirred at ambient temperature for 25 h and then evaporated. During the reaction, the solution becomes brown. The brown residue is dissolved in cyclohexane and then filtered through celite. The filtrate is concentrated so as to give the compound 27 with a yield of 88% (1.52 g; 1.38 mmol) which is used directly for the next step.

$C_{45}H_{88}NO_{16}Si_6$  Chemical formula 27:

Molar mass: 1098.67 g·mol$^{-1}$ $R_f$: 0.57 [DCM/Et$_2$O (90:10)]

Preparation of aminooxyethyl 6-deoxy-6-dihydroxyphosphinylmethylene-α-D-mannopyranosyl-(1→2)-D-mannopyranoside 28

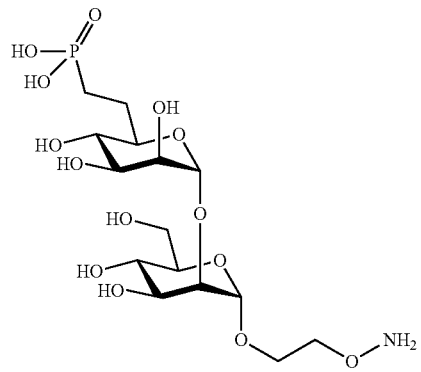

Et$_3$N (7.2 eq, 0.34 ml, 2.4 mmol), TMSCl (7 eq, 0.296 ml, 2.34 mmol) and NaI (7 eq, 350 mg, 2.34 mmol) are added, under nitrogen atmosphere, to a solution of compound 27 (1 eq, 367 mg, 0.33 mmol) in 11 ml of anhydrous CH$_3$CN. After 4 h at ambient temperature, the stirring is stopped. The supernatant is drawn off with a tube and the residual salt is rinsed with anhydrous CH$_3$CN (2×3 ml) and then the solvent is drawn off with a tube. The solvent is evaporated off and the residue obtained is taken up in 7.5 ml of anhydrous methanol containing hydrazine (12 eq, 4.01 mmol, 0.194 ml). The reaction is left to stir overnight. A white precipitate is formed. The residue obtained after evaporation is purified by chromatography on a silica gel column (eluent: 5:4:1 isopropanol/NH$_4$OH/H$_2$O) so as to give the compound 28 with a yield of 64% (103 mg, 0.22 mmol).

$C_{15}H_{30}NO_{14}P$  Chemical formula 28:

Exact weight: 479.37 g·mol$^{-1}$ $R_f$: 0.33 [isopropanol/NH$_4$OH/H$_2$O (5:4:1)]

MS, ESI$^+$ m/z: 480.3 [M+H]$^+$

EXAMPLE 4

Study of the Disaccharide Analog 28 of the Invention, Corresponding to the General Formula (I)

1) Functionalization of a Lysosomal Enzyme, Acid Alpha-Glucosidase (GAA), with the Disaccharide Analog (28)

A compound of interest Ⓨ, namely a lysosomal enzyme, acid alpha-glucosidase (GAA), which can be used for the treatment of Pomp disease or glycogenosis type II[7-8], is functionalized on the oligosaccharide chains with the phosphonate disaccharide analog M6Pn-α(1,2)-Man-Ethyl-oxyamino (28). Pomp disease is representative of the majority of the 53 different lysosomal diseases for which the efficacy of treatment by enzyme replacement therapy depends on CI-M6PR[7-9]. Specifically, this receptor plays a key role in cell internalization of intravenously injected recombinant enzymes and in the intracellular routing thereof to the lysosomes.

Experimental Protocol:

Recombinant human GAA (rhGAA) is produced in the system of CHO eukaryotic cells capable of producing M6P at the end of the glycosylated chains and is purified from the culture medium. The molecular weight of the enzyme is approximately 110 000 Da and it is recognized by a specific anti-human GAA antibody (anti-LYAG, Genetex). The recombinant human GAA can also be produced in the baculovirus/Sf9 insect cell system which does not produce M6P residues and which produces mannosylated oligosaccharide chains.

The rhGAA is then functionalized on the oligosaccharide chains with the phosphonate disaccharide analogs M6Pn-α(1,2)-Man-Ethyloxyamino (28). The functionalization is carried out in two steps: the first step consists in generating aldehyde functions by oxidation of the mannoses which, in the second step, will react with the oxyamine functions present on the ethyloxyamino arm of the analog (28). The enzymes are oxidized by 1 mM NaIO$_4$ for 30 min at 4° C. and then reacted with the disaccharide analogs (100 equivalents for 1 enzyme) for 2 h at 25° C. The functionalized enzymes are obtained after dialysis in order to remove the unreacted analogs.

The coupling (grafting) of the phosphonate disaccharide analog M6Pn-α(1,2)-Man-Ethyloxyamino (28) with the enzymes is represented below:

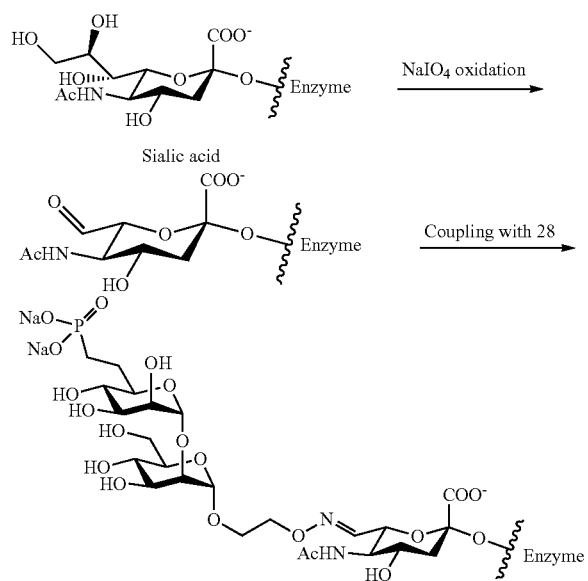

The oxidation of the sialic acid is carried out using sodium periodate.

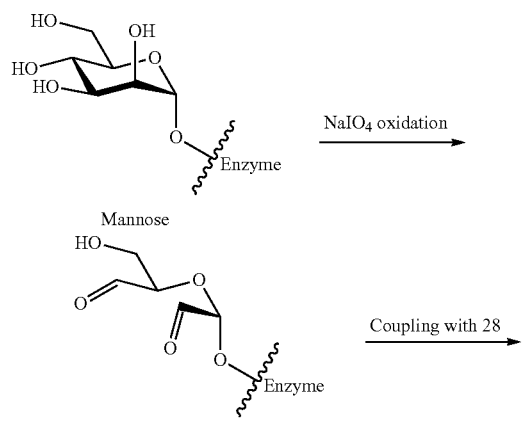

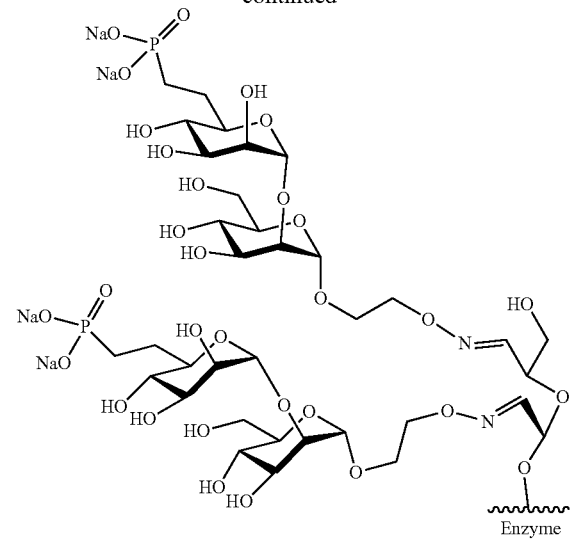

The oxidation of the mannose is carried out using sodium periodate.

2) Affinity for CI-M6PR of the rhGAA Functionalized with M6Pn-α(1,2)-Man-Ethyloxyamino (28)

The conjugate of formula (III), namely the rhGAA functionalized with the phosphonate disaccharide analog M6Pn-α(1,2)-Man-Ethyloxyamino (28), is denoted hereinafter rhGAA-M6Pn-α(1,2)-Man-Ethyloxyamino (28).

The conjugate of formula (III) is evaluated for its affinity with CI-M6PR. The binding affinity of rhGAA and of the rhGAA-M6Pn-α(1,2)-Man-Ethyloxyamino conjugate (28) was evaluated by means of a competitive binding technique with CI-M6PR described in example 2 and compared with the affinity of M6P.

The data indicate a strong affinity for rhGAA-M6Pn-α(1,2)-Man-Ethyloxyamino (28) (conjugate of formula (III)) corresponding to a 50% inhibitory concentration (IC$_{50}$) of $0.55 \cdot 10^{-7}$ M, while the affinity of the rhGAA was $3 \times 10^{-7}$ M, i.e. 5.5 times lower. By comparison, the affinity of M6P is $3 \times 10^{-5}$ M in these same experiments. This result indicates the efficient coupling of several dimannoside analogs of M6P on the glycosylated chains of the enzyme.

3) Internalization of the rhGAA-M6Pn-α(1,2)-Man-Ethyloxyamino Conjugate (28) (Conjugate of Formula (III)) in the Myoblasts of Patients Suffering from the Adult Form of Pomp Disease (FIG. 3)

Experimental Protocol:

The myoblast-type cells originating from an adult patient suffering from Pomp disease are maintained in primary culture.

The catalytic activity of GAA is measured in the cell extracts using the synthetic substrate 4-methylumbelliferyl-α-D-glucopyranoside (4-MUG). This substrate and the molecular weight standards are obtained from Sigma. The GAA activity in the cell extracts (20 μl) is measured in a reaction volume of 75 μl containing 50 mM citric acid, 115 mM K$_2$HPO$_4$, 110 mM KCl, 10 mM NaCl, pH 5.0, with 6 mM 4-MUG, for 10 min at ambient temperature. The reaction is stopped with 75 μl of 0.1 M Tris HCl, pH 8. The fluorescence is read with an excitation filter at 355 nm and an emission filter at 460 nm in 96-well plates, and compared to a standard curve obtained with 4-methylumbelliferone. The catalytic activity is expressed per mg of protein. Mean±standard deviation.

It emerges from FIG. 3 that the grafting of the disaccharides significantly increases the cell penetration of the GAA, the concentration of which is measured through its catalytic activity on the 4-MUG substrate.

Conclusion:

The product of interest, rhGAA functionalized by the addition of disaccharides (28), is more effective in the treatment of an enzymatic deficiency associated with Pomp disease.

4) Study of the Process of Cellular Maturation in Myoblasts from an Adult Patient Suffering from Pomp Disease of the rhGAA-M6Pn-α(1,2)-Man-Ethyloxyamino Conjugate (28) (Conjugate of Formula (III)) (FIG. 4)

The cellular maturation of GAA[10] is carried out in the endosomes and lysosomes by several specific enzymatic cleavages which successively convert the inactive precursor of 110 kDa into intermediate forms of 95 kDa and 76 kDa, then into a mature and active form of 60-70 kDa in the lysosomes[10].

The myoblasts are incubated for 48 h in the presence of 50 nM rhGAA or of the rhGAA-M6Pn-α(1,2)-Man-Ethyloxyamino conjugate (28) (conjugate of formula (III)), then lysed and the proteins are extracted. The cellular maturation of the internalized GAA enzyme in the myoblasts of patients suffering from Pomp disease is studied by the SDS polyacrylamide gel separation technique, followed by immunodetection of the GAA by Western blot with an anti-human GAA antibody (anti-LYAG, Genetex) or an anti-human actin antibody (Invitrogen). The actin is revealed as a control protein indicating that equivalent amounts of proteins are loaded onto the gel. This experiment is representative among two experiments. The thick arrow in FIG. 4 indicates the intermediate form of GAA. The black arrow indicates the mature form of GAA (60-70 kDa).

The mature form of 60 kDa is quantified by considering the band present in the myoblasts originating from a healthy subject to be 100%. The expression of GAA 60 kDa in the patient myoblasts corresponds to 1% of the GAA of a healthy subject and is not increased in the myoblasts treated with rhGAA. Conversely, the treatment with the rhGAA-M6Pn-α(1,2)-Man-Ethyloxyamino conjugate (28) increases the 60-70 kDa band to 47% of the GAA of a healthy subject. These results indicate that the grafting of the disaccharide analogs very strongly promotes the process of intracellular maturation of the rhGAA, resulting in its active form of 60-70 kDa. This activity is important for an application in the treatment of Pomp disease by enzyme therapy, but can also be applicable to all lysosomal diseases.

Conclusion

The functionalization of a lysosomal enzyme with modified dimannosides thus makes it possible to very significantly increase the cellular entry of this enzyme compared with the non-grafted enzyme in cells from a patient suffering from Pomp disease. The functionalization with the dimannoside analogs of M6P makes it possible to facilitate the maturation of the enzyme inside the endosomes and lysosomes compared with the non-functionalized enzyme. This increase in effectiveness associated with the affinity for CI-M6PR can be determined for the diagnostic or therapeutic application of glycoproteins, in particular for enzyme replacement therapy used for lysosomal overload diseases[7-9].

LITERATURE REFERENCES

1. FR patent application No. 14 50588 filed on Jan. 23, 2014;
2. Vidal S et al., Bioorg Med Chem. 10, 4051, (2002);
3. Jeanjean A et al., Bioorg Med Chem. 14, 2575, (2006);
4. Jeanjean A et al., Bioorg Med Chem Lett. 18, 6240, (2008);
5. International application PCT/EP2010/059507;
6. Distler J J et al., J. Biol Chem, 32, 21687, (1991);
7. Desnick, R J, Schuchman E H, Nat Rev Genet 3, 954, (2002);
8. Van der Ploeg A T, Reuser A J, Lancet, 372, 1342, (2008);
9. Hollak, C E, Wijburg F A, J Inherit Metab Dis, 37, 587, (2014);
10. Moreland R J et al., Gene, 491, 25, (2012).

The invention claimed is:

1. A compound having the general formula (I):

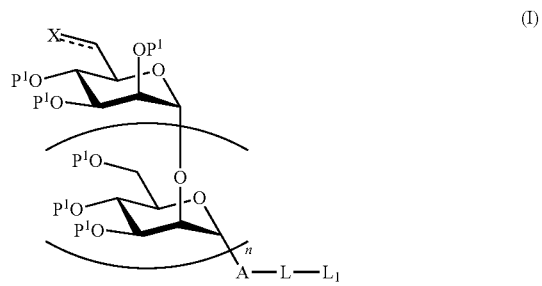

in which:
n is an integer ranging from 1 to 3,
====== represents a single bond or a double bond,
each of the P[1] represents, independently of one another, H, or an acid-labile, base-labile, hydrogen-labile, photo-labile or halogen-labile protecting group, in particular chosen from $(CH_3)_3Si$—; $tBuMe_2Si$—; $C_6H_5CH_2$—; $4\text{-}CH_3OC_6H_5CH_2$—; $o\text{-}NO_2C_6H_5CH_2$—; $CH_3CO$—; $C_6H_5CO$— or $CF_3CO$—;
X represents:
when ====== is a single bond:
the phosphonate group:

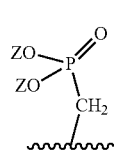

the fluorophosphonate group:

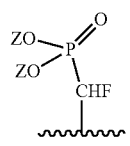

the difluorophosphonate group:

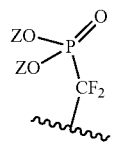

the carboxylate group:

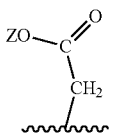

the malonate group:

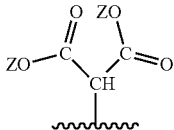

when ==== is a double bond:
the phosphonate group:

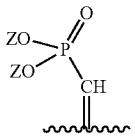

the carboxylate group:

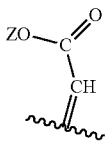

with Z representing, independently of one another, H; a $C_{1-5}$ alkyl; $CF_3CH_2$—; $C_6H_5CH_2$—; $C_6H_5$—; $(CH_3)_3Si$—; an alkali metal chosen from Na, Li or K; an ammonium $NH_4$;

A represents a divalent radical chosen from —O—, —S—, —NH—, —$CH_2$—;

L represents:
—H; —$NH_2$; —$(CH_2)_{n1}$—CH=$CH_2$ or —$(CH_2)_{n1}$—C≡CH with $n_1$ representing an integer ranging from 0 to 4, then in each of these cases, $L_1$ is absent, a substituted or unsubstituted, linear or branched, saturated divalent hydrocarbon-based radical having from 1 to 30 carbon atoms, a substituted or unsubstituted, linear or branched, unsaturated divalent hydrocarbon-based radical having from 2 to 30 carbon atoms, a saturated or unsaturated divalent hydrocarbon-based radical as defined above, in which one or more —$CH_2$—, —CH=CH— and/or —C≡C— groups of the saturated or unsaturated hydrocarbon-based radical is (are) replaced, independently of one another, with an —O— group; —NH— group; —$NR_1$— group with $R_1$ representing a $C_1$-$C_5$ alkyl; —S— group; —CO—NH— group; —NH—CO—O— group; —O—N=CH— group; —CO—NH—N=CH— group; a substituted or unsubstituted, saturated or unsaturated, cyclic or heterocyclic system;

$L_1$ represents:
—$(CH_2)_{n1}$—CH=$CH_2$; —$(CH_2)_{n1}$—C≡CH; —$(CH_2)_{n1}$—$N_3$; —$(CH_2)_{n1}$—SH; —$(CH_2)_{n1}$—$NH_2$; —$(CH_2)_{n1}$—N=C=O; —$(CH_2)_{n1}$—N=C=S; —$(CH_2)_{n1}$—$NHR_1$; —$(CH_2)_{n1}$—$NR_1R_2$; —$(CH_2)_{n1}$-$A_1$-$NH_2$; —$(CH_2)_{n1}$-$A_1$-$NHR_1$; —$(CH_2)_{n1}$-$A_1$-$NR_1R_2$; —$(CH_2)_{n1}$—NHCO—$CH_2$Hal; —$(CH_2)_{n1}$—$COZ_1$; —$(CH_2)_{n1}$-$A_1COZ_1$; —$(CH_2)_{n1}$—O—N=$CH_2$; —$(CH_2)_{n1}$—CO—NH—N=$CH_2$; —$(CH_2)_{n1}$—H; a substituted or unsubstituted, saturated or unsaturated, cyclic or heterocyclic system; a halogen chosen from F, Cl, Br or I; with $n_1$ as defined above, $R_1$ and $R_2$ representing, independently of one another, a $C_1$-$C_5$ alkyl, $A_1$ representing —O—, —NH—, Hal representing Cl, Br or I;

$Z_1$ representing —OH, —$OR_1$, —$NHR_1$, —NH—$NH_2$, —NH—$NHR_1$, —NH—$NR_1R_2$, with $R_1$ and $R_2$ as defined above, a halogen chosen from F, Cl, Br or I.

2. The compound as claimed in claim 1, wherein:

L represents:
—$NH_2$, —$(CH_2)_{n1}$—CH=$CH_2$ or —$(CH_2)_{n1}$—C≡CH, with $n_1$ as defined in claim 1, then in each of these cases, $L_1$ is absent, a substituted or unsubstituted, linear or branched, saturated divalent hydrocarbon-based radical having from 1 to 10 carbon atoms, a substituted or unsubstituted, linear or branched, unsaturated divalent hydrocarbon-based radical having from 2 to 10 carbon atoms, a saturated or unsaturated, divalent hydrocarbon-based radical as defined above, in which one or more —$CH_2$—, —CH=CH— and/or —C≡C— groups of the saturated or unsaturated hydrocarbon-based radical is (are) replaced, independently of one another, with:

an —O— group; —NH— group; —S— group; —CO—NH— group; —NH—CO—O— group; and/or a cyclic or heterocyclic system chosen from:

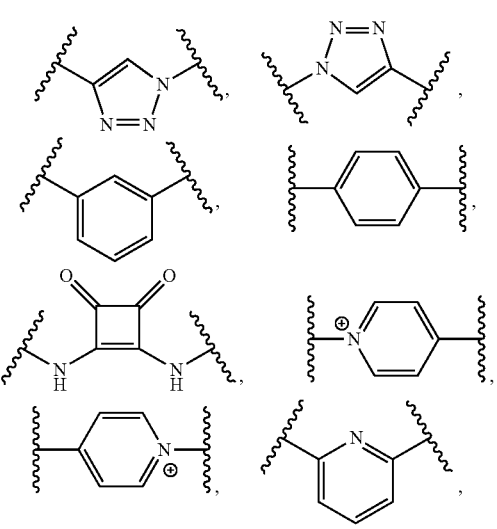

-continued

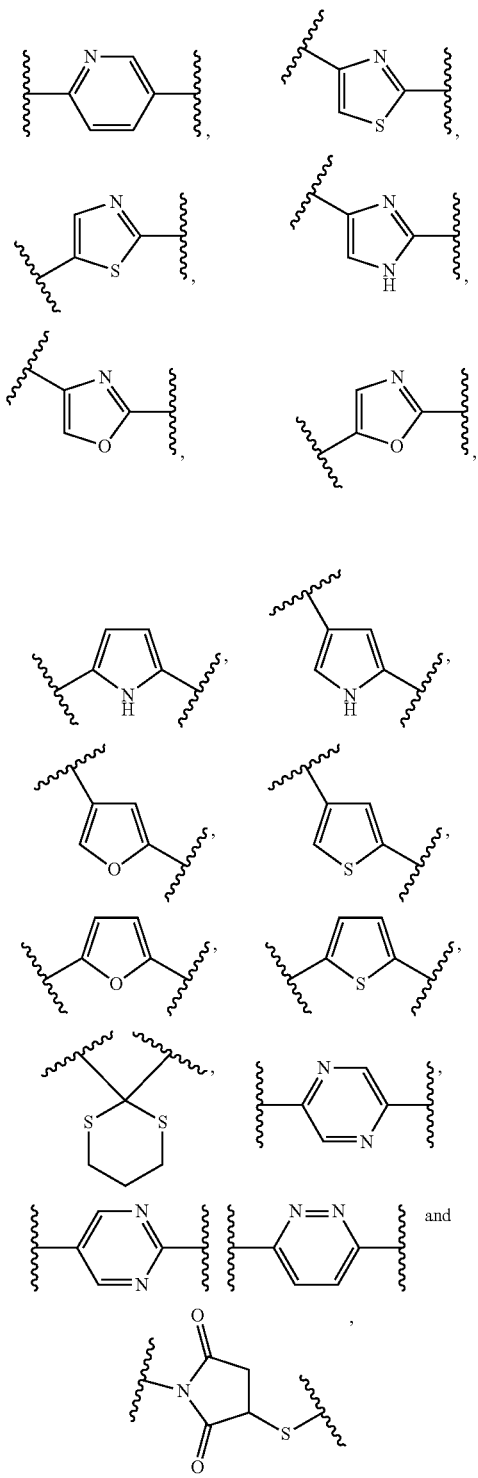

$L_1$ represents:

—$(CH_2)_{n1}$—CH=$CH_2$; —$(CH_2)_{n1}$—C≡CH; —$(CH_2)_{n1}$—$N_3$; —$(CH_2)_{n1}$—SH; —$(CH_2)_{n1}$—$NH_2$; —$(CH_2)_{n1}$—N=C=O; —$(CH_2)_{n1}$—N=C=S; —$(CH_2)_{n1}$—O—$NH_2$; —$(CH_2)_{n1}$—NHCO—$CH_2$Hal; —$(CH_2)_{n1}$—COOH; —$(CH_2)_{n1}$—$COOR_1$; —$(CH_2)_{n1}$—CO—NH—$NH_2$; —$(CH_2)_{n1}$—H; a halogen chosen from F, Cl, Br or I;

a cyclic or heterocyclic system chosen from:

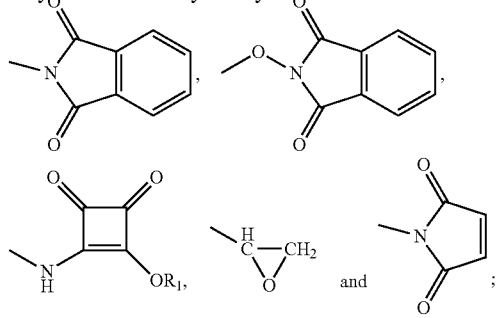

with $n_1$, $R_1$ and Hal as defined in claim 1.

3. The compound as claimed in claim 1, wherein:
the substituent L is chosen from:
—CH=$CH_2$, —C≡CH or —$NH_2$, then in each of these cases, $L_1$ is absent;
—$CH_2$—; —$CH_2$—$CH_2$—; —$(CH_2)_3$—; —$(CH_2)_4$—; —$(CH_2)_5$—; —$CH_2$—$CH_2$—O—$CH_2$—$CH_2$—; —$(CH_2$—$CH_2$—O$)_2$—$CH_2$—$CH_2$—; —$CH_2$—$CH_2$—S—$CH_2$—$CH_2$—; —$CH_2$—$CH_2$—S—$CH_2$—$CH_2$—O—$CH_2$—$CH_2$—;

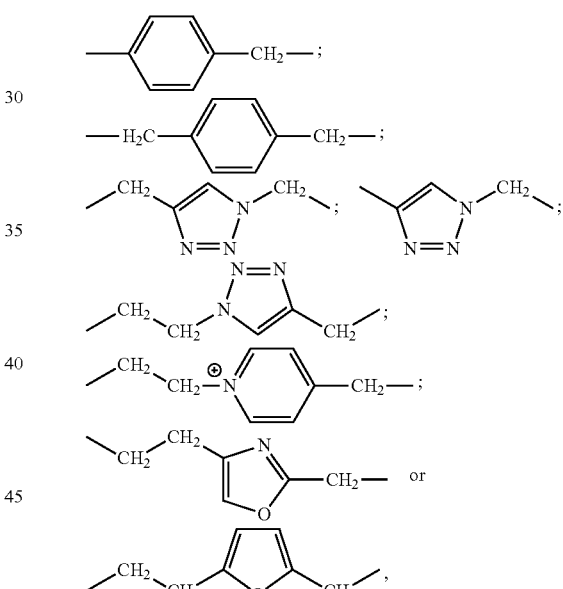

and
the substituent $L_1$ is chosen from:
—CH=$CH_2$; —C≡CH; —$N_3$; —SH; —$NH_2$; —N=C=O; —N=C=S; —O—$NH_2$; —NHCO—$CH_2$Cl; —COOH; —$COOR_1$; —CO—NH—$NH_2$, a halogen chosen from F, Cl, Br or I,
a cyclic or heterocyclic system chosen from:

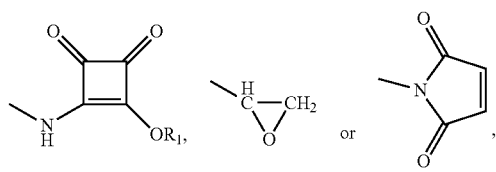

with $R_1$ as defined in claim 1.

4. A process for preparing a compound of formula (I) as claimed in claim 1, wherein the starting compound used is a compound corresponding to the formula (II):

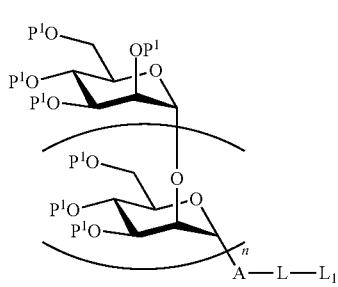

(II)

in which $P^1$, A, L, $L_1$ and n are as defined in claim 1.

5. A conjugate having the general formula (III):

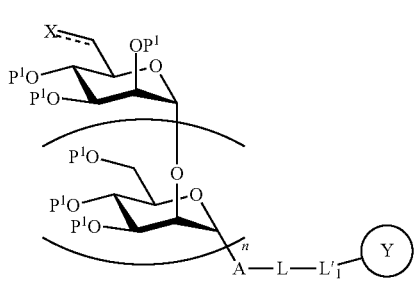

(III)

in which $P^1$, X, n, A and L are as defined in claim 1, $L'_1$ represents the substituent $L_1$ as defined in claim 1 involved in a covalent bond with a functional group borne by a compound of interest

, said compound of interest

being chosen from enzymes, nanoparticles, proteins, antibodies or cytotoxic agents.

6. The conjugate as claimed in claim 5, wherein said conjugate has an $IC_{50}$ affinity for the cation-independent mannose 6-phosphate receptor (CI-M6PR) of at least $10^{-5}$ M, and preferably ranging from $10^{-6}$ to $10^{-9}$ M.

7. The conjugate as claimed in claim 5, wherein the compound of interest

is a lysosomal enzyme or a nanoparticle.

8. A method for therapeutic treatment of a human or animal, wherein the therapeutic treatment is selected from enzyme replacement therapy, photodynamic therapy or cancer treatment comprising administering the conjugate of formula (IIIa)

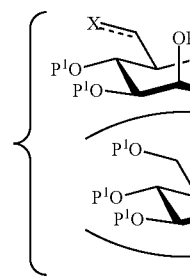

to the human or animal.

9. A method of detecting diseases or ailments associated with an increase or a decrease in CI-M6PR expression in a human or animal comprising administering the conjugate of claim 5 to the human or animal and detecting binding of the conjugate to CI-M6PR.

10. A method of forming at least one covalent bond with at least one functional group borne by a compound of interest (Y), said compound of interest (Y)

being chosen from enzymes, nanoparticles, proteins, antibodies or cytotoxic agents comprising contacting the compound of claim 2 with an enzyme, nanoparticle, protein, antibody or cytotoxic agent.

11. The method as claimed in claim 10, wherein n' compound(s) of formula (I) are present for forming n' covalent bond(s) with n' functional group(s) of the compound of interest (Y), with n' being an integer ranging from 1 to 1000.

12. The method claimed in claim 10, for forming the conjugate of general formula (IIIa):

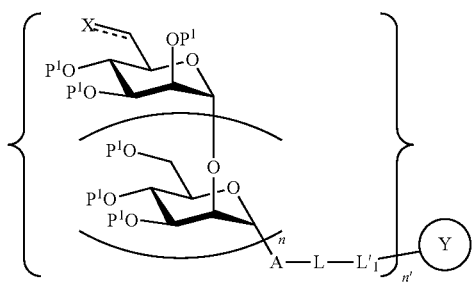

(IIIa)

in which $P^1$, X, n, A, L, $L'_1$ and

Y are as defined in claim 5, n' is as defined in claim 11.

13. A process for preparing a conjugate of formula (III)

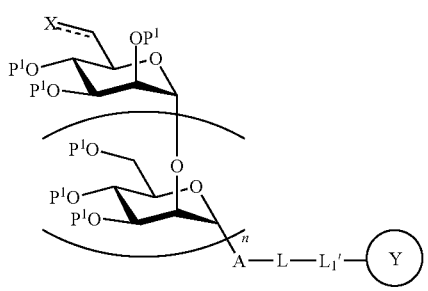

(III)

or a conjugate of formula (IIIa)

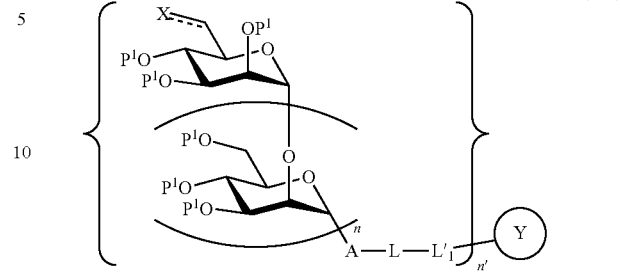

(IIIa)

comprising reacting:

at least one functional group borne by a compound of interest

Y, said compound of interest being chosen from enzymes, nanoparticles, proteins, antibodies or cytotoxic agents, with at least one compound corresponding to the formula (I):

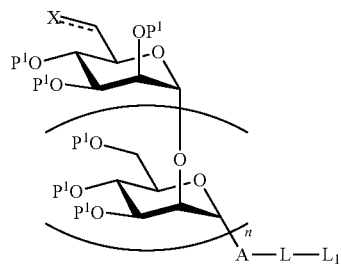

in which $P^1$, X, A and n are as defined in claim 1,

L and $L_1$ are as defined in claim 2 or 3.

* * * * *